US012685541B2

(12) United States Patent
Dillard

(10) Patent No.: US 12,685,541 B2
(45) Date of Patent: Jul. 21, 2026

(54) SURGICAL DRILL COOLING SLEEVE

(71) Applicant: David G. Dillard, Lawrenceville, GA (US)

(72) Inventor: David G. Dillard, Lawrenceville, GA (US)

( * ) Notice: Subject to any disclaimer, the term of this patent is extended or adjusted under 35 U.S.C. 154(b) by 0 days.

(21) Appl. No.: 18/884,712

(22) Filed: Sep. 13, 2024

(65) Prior Publication Data

US 2025/0090177 A1     Mar. 20, 2025

Related U.S. Application Data

(63) Continuation of application No. PCT/US2024/046577, filed on Sep. 13, 2024.

(60) Provisional application No. 63/582,612, filed on Sep. 14, 2023.

(51) Int. Cl.
*A61B 17/16* (2006.01)

(52) U.S. Cl.
CPC ...... *A61B 17/1633* (2013.01); *A61B 17/1644* (2013.01); *A61B 2017/1651* (2013.01)

(58) Field of Classification Search
CPC . A61B 17/16; A61B 17/1613; A61B 17/1615; A61B 17/1617; A61B 17/162; A61B 17/1622; A61B 17/1624; A61B 17/1626; A61B 17/1628; A61B 17/1631; A61B 17/1633; A61B 17/1644; A61B 17/3421; A61B 17/3423; A61B 2017/1651; A61B 2017/3433; A61B 2017/3445; A61B 2017/3447
See application file for complete search history.

(56) References Cited

U.S. PATENT DOCUMENTS

| | | | | |
|---|---|---|---|---|
| 8,641,609 | B2 * | 2/2014 | Hestad ............... | A61B 17/0206 600/215 |
| 10,413,305 | B2 * | 9/2019 | Magno ............... | A61B 17/1631 |
| 11,207,083 | B2 * | 12/2021 | Magno ............... | A61B 17/1644 |
| 12,114,846 | B2 * | 10/2024 | Walen ................ | A61B 17/3421 |
| 12,337,101 | B2 * | 6/2025 | Kokhanenko .......... | A61B 1/127 |
| 2009/0105546 | A1 * | 4/2009 | Hestad ............... | A61B 17/3421 600/245 |

(Continued)

FOREIGN PATENT DOCUMENTS

| | | | | |
|---|---|---|---|---|
| CA | 2184892 A | | 7/1996 | |
| CN | 108618826 A | * | 10/2018 | ..... A61B 17/320758 |

(Continued)

OTHER PUBLICATIONS

International Search report and Written Opinion in PCT pplication No. PCT/US2024/046577.

*Primary Examiner* — Eric S Gibson

(74) *Attorney, Agent, or Firm* — Bradley Arant Boult Cummings LLP; Daniel E. Sineway

(57)     ABSTRACT

A cylindrical sleeve device can be attached or secured to a surgical drill. The sleeve can include a drill coupler, an intermediary section, and a sleeve body. The sleeve can include multiple internal channels. The internal channels can include drill channel, which can be circular and located at the center of the sleeve. The drill channel can be configured to receive a surgical drill. The internal channels can include a suction channel and/or a cooling channel. The suction channel and/or cooling channel can be concentrically positioned relative the drill channel.

18 Claims, 17 Drawing Sheets

(56) References Cited

U.S. PATENT DOCUMENTS

| | | | |
|---|---|---|---|
| 2017/0007295 A1* | 1/2017 | Geisz .................. | A61B 17/3421 |
| 2017/0136555 A1 | 5/2017 | Best et al. | |
| 2018/0055536 A1* | 3/2018 | Geisz ................. | A61B 17/3417 |
| 2018/0271544 A1* | 9/2018 | Magno .............. | A61B 17/1644 |
| 2019/0365389 A1* | 12/2019 | Magno .............. | A61B 17/1644 |
| 2021/0236749 A1* | 8/2021 | Kokhanenko ...... | A61B 17/3462 |
| 2021/0321999 A1* | 10/2021 | Walen ................... | A61B 90/98 |
| 2022/0346809 A1 | 11/2022 | Cushen et al. | |
| 2025/0090177 A1* | 3/2025 | Dillard .............. | A61B 17/1644 |

FOREIGN PATENT DOCUMENTS

| | | | | |
|---|---|---|---|---|
| CN | 210931657 U | | 7/2020 | |
| CN | 218922713 U | | 4/2023 | |
| EP | 3378418 A1 | * | 9/2018 | ..... A61B 17/320758 |
| EP | 3378418 B1 | * | 10/2019 | ........ A61B 17/1633 |
| EP | 3873351 B1 | * | 9/2023 | ........ A61B 17/0218 |
| EP | 4268759 A2 | * | 11/2023 | ........ A61B 17/0218 |
| ES | 2765974 T3 | * | 6/2020 | ........ A61B 17/1633 |
| JP | 2018158095 A | * | 10/2018 | ........ A61B 17/1633 |
| JP | 6877811 B2 | * | 5/2021 | ........ A61B 17/1631 |
| JP | 2022506220 A | * | 1/2022 | ........ A61B 17/0218 |
| WO | WO-2020036498 A1 | * | 2/2020 | ........ A61B 17/3474 |
| WO | WO-2020036499 A1 | * | 2/2020 | ............. A61B 1/313 |
| WO | WO-2020092080 A1 | * | 5/2020 | ............ A61B 90/98 |
| WO | WO-2024134602 A1 | * | 6/2024 | ........ A61B 17/3474 |
| WO | WO-2025059439 A1 | * | 3/2025 | ........ A61B 17/1633 |

* cited by examiner

100

103

109

106

1100

1115

1127

1130

SURGICAL DRILL COOLING SLEEVE

PRIORITY TO RELATED APPLICATIONS

This application is a continuation of and claims the benefit of, and priority to, PCT/US24/46577, filed on Sep. 13, 2024, entitled "Surgical Drill Cooling Sleeve," and U.S. Provisional Patent Application No. 63/582,612, filed on Sep. 14, 2023, entitled "Surgical Drill Cooling Sleeve," the disclosure of which are incorporated herein by reference in its entirety.

TECHNICAL FIELD

The present systems and processes relate generally to bone drills.

BACKGROUND

Surgical drills are used in a variety of medical procedures that require bone to be drilled. In particular, surgical drills are used for a variety of nasal, sinus, ear, and throat procedures such as septoplasties and rhinoplasties. However, surgical drills can produce enormous amounts of heat during operation. Surgical drills can become so hot that a medical professional operating the drill may have to pause use of the drill during procedures, causing procedures to take longer and possibly introduce complications. Additionally, surgical drills can cause debris, such as bone, mucus, saliva, or other bodily debris, to accumulate at a surgical site. Such debris can crowd the surgical site and prevent medical professionals from having a complete view of the surgical site.

Therefore, there is a long-felt but unresolved need for a device that can remove the excess heat produced by a surgical drill. Further, there is an additional need for a device that can remove bodily debris from a surgical site.

BRIEF SUMMARY OF THE DISCLOSURE

Briefly described, and according to one embodiment, aspects of the present disclosure generally relate to a sleeve that is attachable or otherwise securable to a surgical drill. The sleeve can include a drill coupler and a sleeve body. The drill coupler can be located at the top of the sleeve, and the sleeve body can be located below the drill coupler. The sleeve can include an intermediary section connecting the drill coupler and the sleeve body. The intermediary section can have an upside-down conical frustum shape (e.g., a truncated cone) with a top end and a bottom end.

The sleeve can include a sleeve body. The sleeve body can have a variable outer diameter (and/or a variable inner diameter). For example, the sleeve body can have a tapered cylinder shape. Continuing with this example, the diameter at the top of the sleeve body can be greater than the diameter at the bottom of the sleeve body.

The sleeve can include multiple internal channels, such as a drill channel, a suction channel, and/or a cooling channel. The drill channel can be located at the center of the sleeve. The drill channel can have a generally circular cross-sectional shape. The suction channel can be located outside of and adjacent to the drill channel. The suction channel can be a channel having a generally concentric cross-sectional shape and/or can be a concentric channel around the outside of the drill channel. The cooling channel can be located outside of and adjacent to the suction channel. The cooling channel can be a concentric channel around the outside of the suction channel (or the cooling channel can be a channel that is otherwise concentrically located relative to the suction channel).

Alternatively, the cooling channel can be located outside of and adjacent to the drill channel (e.g., the cooling channel can be a concentric channel around the outside of the drill channel), and the suction channel can be located outside of and adjacent to the cooling channel (e.g., the suction channel can be a concentric channel around the outside of the cooling channel).

The drill channel can include a proximal opening located at the top of the sleeve and a distal opening located at the bottom of the sleeve. The sleeve can be secured to (or securable to) the surgical drill such that the sleeve remains attached to the surgical drill throughout a procedure. For example, once a surgical drill has been inserted into the proximal opening and through the drill channel, the drill bit of the surgical drill can extend outwardly through the distal opening such that the drill bit can be used in a procedure. The sleeve can be detachably attachable to the surgical drill (e.g., the sleeve can be attached to and/or detached from the surgical drill).

The suction channel can be in fluid communication (e.g., connected to, attached to, connected via a channel) with a suction outlet, which can comprise a suction connection point located at the top of the sleeve. The suction connection point can be connectable or otherwise attachable to a suction device, which can therefore enable the suction device to remove bone or other bodily debris from a surgical site. The suction channel can include a suction inlet at the bottom of the sleeve. The suction inlet, suction channel, and suction outlet can facilitate the removal of bone and other debris from a surgical site during a procedure via the sleeve.

The cooling channel can include a fluid inlet, which can include a fluid inlet connection point, and a fluid outlet, which can include a fluid outlet connection point. The fluid inlet connection point and/or the fluid outlet connection point can be connected to a cooling system (e.g., a recirculating cooling system, such as a heat pump or compressor). The cooling fluid can be or include any refrigerant (e.g., gas or liquid) capable of removing heat from the sleeve. The cooling fluid can be appropriate for medical use (e.g., nitrous oxide, Freon, liquid helium). The cooling fluid can enter the sleeve through the fluid inlet connection point and can exit the sleeve through the fluid outlet connection point. As the cooling fluid moves through the cooling channel, heat produced by a surgical drill can be transferred to the cooling fluid via heat transfer, and the heated cooling fluid can then flow out of the sleeve, thus removing at least some of the heat produced by the surgical drill.

The configuration of the cooling channel and/or suction channel can further vary. For example, the cooling channel can be or include a loop channel with an inlet end and an outlet end. As a non-limiting example, the inlet end and the outlet end of the cooling channel can each be or include a half-circular concentric channel (e.g., the inlet end can be one half of a concentric circular channel and the outlet end can be the other half of a concentric circular channel). The cooling channel can have a generally helical shape. Alternatively or in addition, the cooling channel can have a generally double-helical shape (e.g., one side of the double helix can guide an inflow of the cooling fluid and the other side of the double helix can guide an outflow of the cooling fluid).

Alternatively or in addition, the cooling channel can include multiple flow paths, which can include one or more axially-extending flow paths and one or more loops (e.g., rotations about a portion of the sleeve, circumferentially-extending flow paths connecting the one or more axially-extending channels). For example, the cooling channel can include two axially-extending flow paths, and the axially-extending flow paths can be fluidly connected to one or more loops, which can wrap around at least a portion of the drill channel (e.g., extend in an at least partially circumferential direction) to fluidly connect the two axially-extending flow paths. The loops can wrap around the suction channel. The cooling channel can be or include an inner channel and outer channel. The inner channel and the outer channel can connect (e.g., be in fluid communication with one another) at or near the bottom of the sleeve.

These and other aspects, features, and benefits of the disclosed technology will become apparent from the following detailed written description of the preferred embodiments and aspects taken in conjunction with the following drawings, although variations and modifications thereto may be effected without departing from the spirit and scope of the novel concepts of the disclosure.

BRIEF DESCRIPTION OF THE FIGURES

The accompanying drawings illustrate one or more embodiments and/or aspects of the disclosure and, together with the written description, serve to explain the principles of the disclosure. Wherever possible, the same reference numbers are used throughout the drawings to refer to the same or like elements of an embodiment, and wherein.

DETAILED DESCRIPTION

Figure 1:
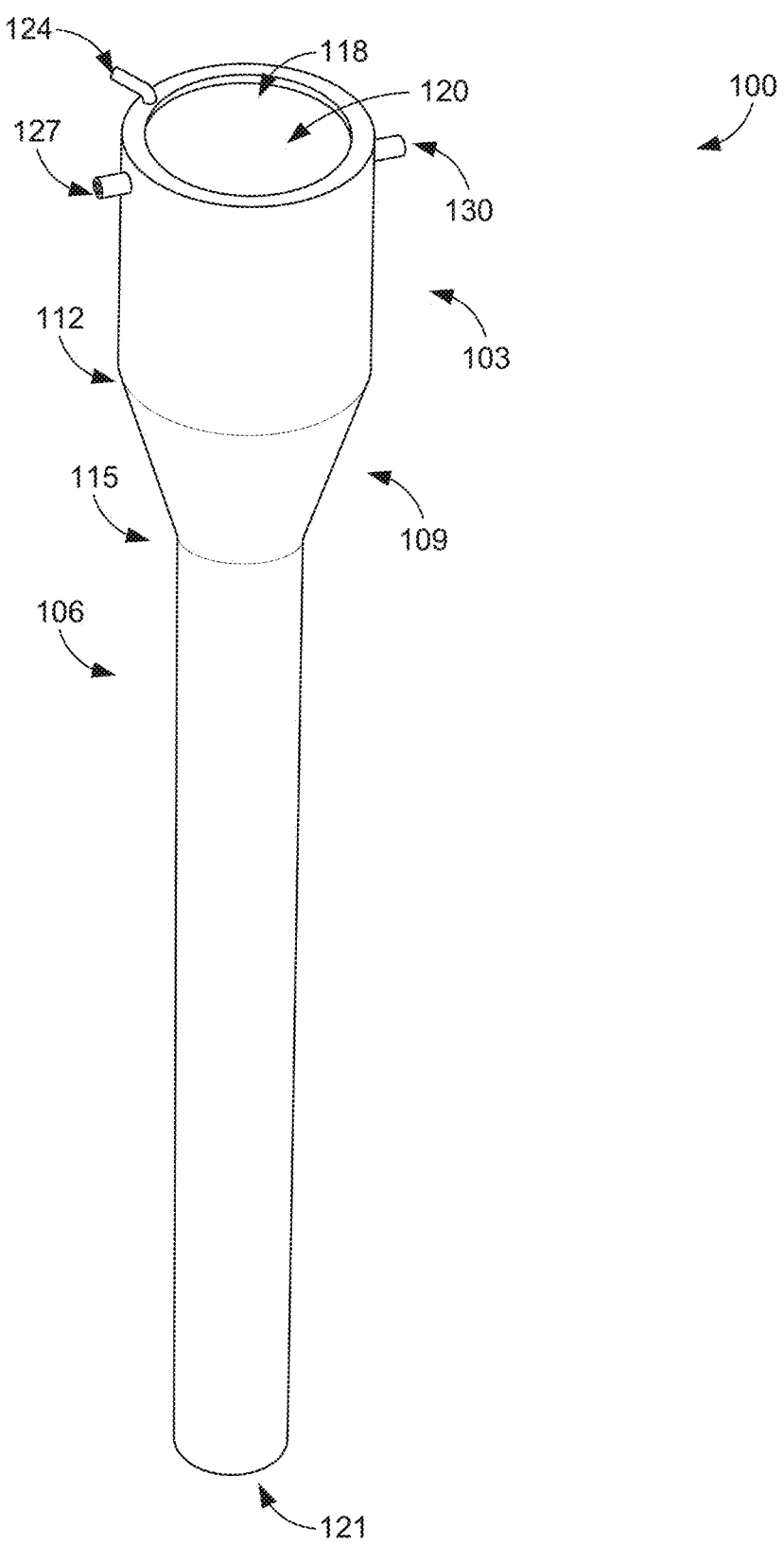
FIG. 1 illustrates a perspective view of an exemplary, in accordance with the disclosed technology.

For the purpose of promoting an understanding of the principles of the present disclosure, reference will now be made to the embodiments illustrated in the drawings and specific language will be used to describe the same. It will, nevertheless, be understood that no limitation of the scope of the disclosure is thereby intended; any alterations and further modifications of the described or illustrated embodiments, and any further applications of the principles of the disclosure as illustrated therein are contemplated as would normally occur to one skilled in the art to which the disclosure relates. All limitations of scope should be determined in accordance with and as expressed in the claims.

Throughout this disclosure, various aspects of the disclosed technology can be presented in a range format (e.g., a range of values). It should be understood that such descriptions are merely for convenience and brevity and should not be construed as an inflexible limitation on the scope of the disclosed technology. Accordingly, the description of a range should be considered to have specifically disclosed all the possible subranges as well as individual rational numerical values within that range. For example, a range described as being "from 1 to 6" includes the values 1, 6, and all values therebetween. Likewise, a range described as being "between 1 and 6" includes the values 1, 6, and all values therebetween. The same premise applies to any other language describing a range of values. That is to say, the ranges disclosed herein are inclusive of the respective endpoints, unless otherwise indicated.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

In the following description, numerous specific details are set forth. But it is to be understood that embodiments of the disclosed technology may be practiced without these specific details. In other instances, well-known methods, structures, and techniques have not been shown in detail in order not to obscure an understanding of this description. References to "one embodiment," "an embodiment," "example embodiment," "some embodiments," "certain embodiments," "various embodiments," etc., indicate that the embodiment(s) of the disclosed technology so described may include a particular feature, structure, or characteristic, but not every embodiment necessarily includes the particular feature, structure, or characteristic. Further, repeated use of the phrase "in one embodiment" does not necessarily refer to the same embodiment, although it may.

Throughout the specification and the claims, the following terms take at least the meanings explicitly associated herein, unless the context clearly dictates otherwise. The term "or" is intended to mean an inclusive "or." Further, the terms "a," "an," and "the" are intended to mean one or more unless specified otherwise or clear from the context to be directed to a singular form.

Unless otherwise specified, the use of the ordinal adjectives "first," "second," "third," etc., to describe a common object, merely indicate that different instances of like objects are being referred to and are not intended to imply that the objects so described should be in a given sequence, either temporally, spatially, in ranking, or in any other manner.

Whether a term is capitalized is not considered definitive or limiting of the meaning of a term. As used in this document, a capitalized term shall have the same meaning as an uncapitalized term, unless the context of the usage specifically indicates that a more restrictive meaning for the capitalized term is intended. However, the capitalization or lack thereof within the remainder of this document is not intended to be necessarily limiting unless the context clearly indicates that such limitation is intended.

OVERVIEW

Aspects of the present disclosure generally relate to a sleeve that can be attached or secured to a surgical drill, including but not limited to a rotating surgical drill or an ultrasonic surgical drill. The sleeve can include a drill coupler and a sleeve body. The drill coupler can be located at or near (e.g., proximate) the top of the sleeve, and the sleeve body can be located below the drill coupler. The drill coupler and the sleeve body can both have a generally cylindrical cross-sectional shape. The drill coupler can have a larger diameter than the diameter of at least a portion of the sleeve body. As a non-limiting example, the diameter of the sleeve body can be 3 millimeters or less. The sleeve body can have an extended (e.g., long, a large length-to-diameter ratio) cylindrical shape and be several times longer than the drill coupler. The sleeve can include an intermediary section connecting the drill coupler and the sleeve body. The intermediary section can have an upside-down conical frustum-like shape (e.g., a truncated cone) with a top end and a bottom end. The top end of the intermediary section can have a diameter larger than the diameter of the bottom end. Alternatively, the shape of the overall sleeve can be a generally upside-down conical frustum-like shape.

The sleeve body can have a substantially constant outer diameter. Alternatively, the sleeve body can be tapered. Said another way, the sleeve body can have a tapered cylinder shape. For example, the diameter at the top of the sleeve body can be greater than the diameter at the bottom of the sleeve body. The sleeve, including the drill coupler, the sleeve body, and the intermediary section, can have a small diameter (e.g., 20 millimeters or less) such that the sleeve can be inserted into a very small surgical incision. The sleeve can have a small diameter such that the sleeve can be used on a small surgical site or for a surgery requiring precision, including but not limited to skull (e.g., ear, nose, throat, sinus, or neurological) surgeries or spinal surgeries.

The sleeve can include multiple internal channels. The internal channels can include a drill channel, a suction channel, and/or a cooling channel. A drill channel can be circular and/or can be located at or near the axial center of the sleeve. The suction channel can have a generally circular cross-sectional shape and/or can be concentrically located outside of, and adjacent to, the drill channel (e.g., the suction channel can be a concentric channel located around the outside of the drill channel). The cooling channel can be located outside of, and adjacent to, the suction channel (e.g., the cooling channel can be a concentric channel located around the outside of the suction channel).

Alternatively, the cooling channel can be located outside of, and adjacent to, the drill channel (e.g., the cooling channel can be a concentric channel around the outside of the drill channel). The suction channel can be located outside of, and adjacent to, the cooling channel (e.g., the suction channel can be a concentric channel around the outside of the cooling channel).

The drill channel can include a proximal opening located at the top of the sleeve and a distal opening located at the bottom of the sleeve. The proximal opening can be an opening at the top of the sleeve for a surgical drill to be inserted into the sleeve. The drill channel can extend through the sleeve from the proximal opening at the top of the sleeve to the distal opening at the bottom of the sleeve. The sleeve can be secured to (or securable to) the surgical drill such that the sleeve remains attached to the surgical drill throughout a procedure. For example, once a surgical drill has been inserted into the proximal opening and through the drill channel, the drill bit of the surgical drill can extend outwardly through the distal opening such that the drill bit can be used in a procedure. The sleeve can be detachably attachable to the surgical drill.

The suction channel can be in fluid communication (e.g., connected to, attached to, connected via a channel) with a suction outlet, which can include a suction connection point located at the top of the sleeve. The suction connection point can be connectable or otherwise attachable to a suction device, which can be connected to or attached to the suction connection point. Suction provided by the suction device, which can be connected to the suction connection point via a hose or tube, can be used to remove bone, mucus, saliva, or other debris from a surgical site. The suction channel can include a suction inlet at the bottom of the sleeve. The suction inlet can allow for bone and other debris to be sucked up into the sleeve and be removed from a surgical site during a procedure.

The cooling channel can include a fluid inlet, which can include a fluid inlet connection point, and a fluid outlet, which can include a fluid outlet connection point. The fluid inlet connection point and/or the fluid outlet connection point can be connected to, or otherwise in fluid communication with, a cooling system (e.g., a recirculating system, such as a heat pump or compressor). The cooling fluid can be or include any refrigerant (e.g., gas or liquid) capable of removing heat from the sleeve. The cooling fluid can be appropriate for medical use (e.g., nitrous oxide, Freon, liquid helium). The cooling fluid can enter the sleeve through the fluid inlet connection point and exit the sleeve through the fluid outlet connection point. As the cooling fluid moves through the cooling channel, heat produced by the surgical drill can be transferred to the cooling fluid via heat transfer, and the heated cooling can then flow out of the sleeve, thus removing at least some of the heat produced by the surgical drill.

The configuration of the cooling channel and/or the suction channel can further vary. For example, the cooling channel can be or include a loop channel with an inlet end and an outlet end. The inlet end and the outlet end of the gas cooling channel can each be or include a half-circular concentric channel (e.g., the inlet end can be one half of a concentric circular channel and the outlet end can be the other half of a concentric circular channel). The inlet end can begin at the fluid inlet connection point and extend straight down one side of the sleeve. Continuing this example, at some point along the length of the sleeve body (e.g., halfway down the sleeve body), the inlet end can cross over the width of the sleeve body to the opposite side of the sleeve. After crossing over the width of the sleeve body, the inlet end can extend to the bottom of the sleeve body. The inlet end can connect to the outlet end (e.g., the side of the cooling channel located on the opposite side of the sleeve) at the bottom of the sleeve body. The outlet end can extend straight up one side of the sleeve. At a particular point along the length of the sleeve body (e.g., halfway up the sleeve body), the outlet end can cross over the width of the sleeve body to the opposite side of the sleeve. After crossing over the width of the sleeve body, the outlet end can extend straight to the top of the drill coupler and connect with the fluid outlet connection point (see, e.g., FIGS. 9 and 10).

The cooling channel can have a generally helical shape. For example, the cooling channel can wrap around the drill channel. Alternatively or in addition, the generally helically shaped cooling channel can wrap around the suction channel. The cooling channel can have a generally double-helical shape (e.g., one side of the double helix can guide an inflow of the cooling fluid and the other side of the double helix can guide an outflow of the cooling fluid).

The cooling channel can include multiple loops (e.g., the cooling channel can extend up and down the length of the sleeve in a zig-zagging pattern). For example, a cooling channel loop can start at the fluid inlet connection point (e.g., be in fluid communication with the fluid inlet connection point) and can include a flow path extending axially downward along the sleeve toward the bottom of the sleeve body. Continuing with this example, the cooling channel loop can include a bend and can reverse directions (e.g., turn approximately 180°) such that the flow path now extends axially upward along the sleeve toward the top of the sleeve body and extend straight up the sleeve to the top of the sleeve body. This pattern can be repeated any number of times to provide a zig-zagging flow path up and down the length of the sleeve with various sections extending in a generally axial direction and a bend connecting adjacent axially-extending section. The cooling channel loop can eventually connect with, or otherwise be in fluid communication with, the fluid outlet connection point.

Alternatively or in addition, the cooling channel can include two axially-extending flow paths, which can each extend in an at least partially axial direction (e.g., a generally axial direction) along a portion of the length of the sleeve body. One axially-extending flow path can connect to, or otherwise be in fluid communication with, the fluid inlet connection point, and the other axially-extending flow path can connect to, or otherwise be in fluid communication with, the fluid outlet connection point. The axially-extending flow paths can be approximately parallel. Alternatively, the axially-extending flow paths can be angled with respect to one another. The axially-extending flow paths can be in fluid communication with one or more loops that extend in an at least partially circumferential direction (e.g., a generally circumferential direction). For example, the one or more loops can wrap or arc around the drill channel to fluidly connect the two axially-extending flow paths. As another example, the multiple loops can wrap around the circular concentric suction channel.

Alternatively or in addition, the cooling channel can be or include an inner channel and outer channel. The outer channel can be located outside of, and adjacent to, the inner channel. The inner channel and outer channel can be concentric. The inner channel and the outer channel can fluidly connect at or near the bottom of the sleeve. For example, a wall separating the inner channel from the outer channel can terminate to provide a passage between the inner channel and the outer channel. The inner channel can be connected to the fluid inlet connection point, and the outer channel can be connected to the fluid outlet connection point. Alternatively, the outer channel can be connected to the fluid inlet connection point, and the inner channel can be connected to the fluid outlet connection point.

The sleeve can be manufactured by 3D printing methods using any 3D printing material appropriate for medical use. Alternatively or in addition, the sleeve can be formed by laser etching. The drill channel, the cooling channel, and the suction channel, including their respective inlets and outlets, can be formed by laser etching. The laser etched channels, including the drill channel, the cooling channel, and the suction channel, can each have a small diameter. Laser etching the channels can allow for the sleeve to have a sufficiently small diameter (e.g., a sufficiently small diameter to allow the sleeve to be used on small surgical sites or inserted into small incisions).

Alternatively or in addition, the sleeve can be attached or secured to an endoscope or other surgical device. The sleeve can be attached or secured to any surgical or medical device that produces excess heat. As an example, the sleeve can be attached or secured to an endoscope and remove excess heat produced by the endoscope via the cooling channel. Alternatively or in addition, the sleeve can be attached or secured to any surgical device that causes an accumulation of bodily debris (e.g., bone, mucus, saliva, blood) at the surgical site. As an example, the sleeve can be attached or secured to a surgical device that causes an accumulation of bodily debris at the surgical site and remove the bodily debris produced by the surgical device via the suction channel. The sleeve can be integrated with a surgical device, such as a surgical drill or endoscope. As an example, the sleeve can be integrated with the shaft of a surgical drill. The drill channel can be a concentric channel surrounding the shaft of the surgical drill. The cooling channel and the suction channel can be laser etched in the drill shaft.

EXAMPLES OF THE DISCLOSED TECHNOLOGY

Referring now to the figures, for the purposes of example and explanation of the fundamental components and methods of production for the disclosed device, reference is made to FIG. 1, which illustrates an exemplary device. As will be understood and appreciated, the exemplary device shown in FIG. 1 represents merely one approach or embodiment of the present device, and other aspects are used according to various embodiments of the present device. Aspects of the various embodiments disclosed herein can be combined to into various, additional embodiments.

FIG. 1 shows an exemplary orthopedic bone drill sleeve 100 (the "sleeve 100"). The sleeve 100 can include a drill coupler 103 and a sleeve body 106. The drill coupler 103 can be located at the top of the sleeve 100, and the sleeve body 106 can be located below the drill coupler 103. The drill coupler 103 and the sleeve body 106 can both have a cylindrical shape. The drill coupler 103 can have a larger diameter than the diameter of the sleeve body 106. The diameter of the sleeve body 106 can be 3 millimeters or less. The sleeve body 106 can have a long cylindrical shape and be several times longer than the drill coupler 103.

The sleeve 100 can include an intermediary section 109 between the drill coupler 103 and sleeve body 106. The intermediary section 109 can connect the bottom end of the drill coupler 103 to the top end of the sleeve body 106. The intermediary section 109 can have an upside-down conical frustum shape (e.g., a truncated cone) with a top end 112 and a bottom end 115. The top end 112 of the intermediary section 109 can have a diameter larger than the bottom end 115. As an example, the drill coupler 103 can have a larger diameter than the diameter of the sleeve body 106. Continuing this example, the top end 112 of the intermediary section 109 can have a diameter equal to the diameter of the drill coupler 103. In this example, the bottom end 115 of the intermediary section 109 can have a diameter equal to the diameter of the sleeve body 106.

The sleeve 100 can include a proximal opening 118. The proximal opening 118 can be located at the top of the drill coupler 103. The proximal opening 118 can be an opening at the top of the drill coupler 103 for a surgical drill to be inserted into the sleeve 100. The proximal opening 118 forms a drill channel 120 that can extend through the drill coupler 103, the intermediary section 109, and the sleeve body 106. The drill coupler 103 can secure the sleeve 100 to the surgical drill such that the sleeve 100 remains attached to the surgical drill throughout a procedure. The surgical drill can be attached to and/or detached from the drill coupler 103.

The sleeve 100 can include a distal opening 121. The distal opening 121 can be located at the end of the sleeve body 106. The distal opening 121 can form a continuous drill channel 120 with the proximal opening 118 (e.g., the distal opening 121 can be one end of a drill channel 120 formed with the proximal opening 118). In this example, once a surgical drill has been inserted into the proximal opening 118 and through the drill channel 120, the drill bit of the surgical drill can exit the distal opening 121 such that the drill bit can be used in a procedure.

The sleeve 100 can include a suction connection point 124. The suction connection point 124 can be provide suction (e.g., a pressure differential) at a surgical site via a suction device (e.g., a medical device able to provide suction during a procedure). The suction connection point 124 can be used to connect a hose or tube from a suction device to the sleeve 100. The suction connection point 124 can be any appropriate connection point for connecting a tube, hose, or suction device to the sleeve 100 (e.g., attaching or securing a tube, hose, or suction device to the sleeve 100 such that the tube, hose, or suction device can remain attached or secured to the sleeve 100 throughout a procedure). The suction provided by a suction device connected to the suction connection point 124 via a hose or tube can be used to remove bone, mucus, saliva, or other debris from a surgical site. The suction connection point 124 can be located at the top of the drill coupler 103. The suction connection point 124 can be located next to the proximal opening 118.

The sleeve 100 can include both a fluid inlet connection point 127 and a fluid outlet connection point 130. The fluid inlet connection point 127 can provide cooling fluid to the sleeve 100. The cooling fluid can be or include any refrigerant or fluid (e.g., gas or fluid) appropriate for medical use that can remove heat from the sleeve 100 (e.g., nitrous oxide, Freon, liquid helium). Cooling fluid can enter the sleeve 100 through the fluid inlet connection point 127 and exit the sleeve through the fluid outlet connection point 130. Both the fluid inlet connection point 127 and the fluid outlet connection point 130 can be used to connect a hose or tube from a gas source (e.g., a gas tank, gas supply line) to the sleeve 100. Both the fluid inlet connection point 127 and the fluid outlet connection point 130 can be any appropriate connection point for connecting a tube or hose (e.g., attaching or securing a tube or hose to the sleeve 100 such that the tube or hose can remain attached or secured to the sleeve 100 throughout a procedure). Both the fluid inlet connection point 127 and the fluid outlet connection point 130 can be located at the top of the drill coupler 103.

Figure 2:
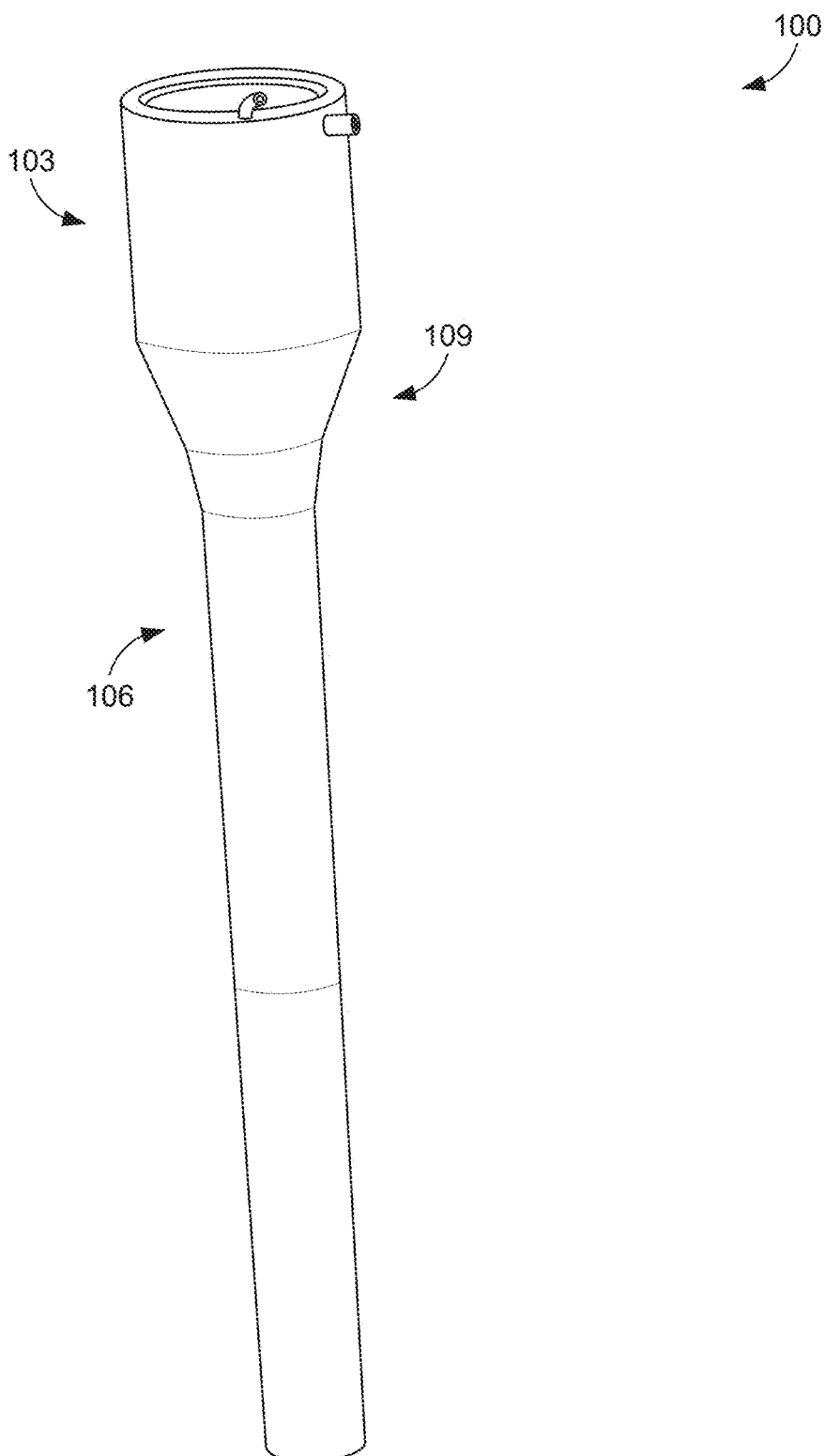
FIG. 2 illustrates a perspective view of an exemplary sleeve, in accordance with the disclosed technology.

Referring now to FIG. 2, a perspective view of an exemplary sleeve 100 is shown. The sleeve 100 can include multiple parts that can be separately manufactured and assembled together to form the sleeve 100. As an example, both the sleeve body 106 and the intermediary section 109 can include two or more parts each that are assembled together. The separate parts of the sleeve 100 can be manufactured by 3D printing methods. The sleeve parts (e.g., drill coupler 103, sleeve body 106, intermediary section 109) can be manufactured with nylon (or any other 3D printing material appropriate for medical use) using 3D printing. The sleeve parts can be manufactured using 3D metal printing with any suitable metal (e.g., titanium, steel, aluminum cobalt chrome, tungsten, nickel-based alloy). As an example, laser etching can be used to form the interior channels of the sleeve 100. The sleeve 100 can include additional outside parts for rigidity or insulation. For example, a steel piece can be attached to the outside of the sleeve 100 for rigidity. As an example, an insulating material or heat-tolerant plastic (e.g., epoxy, nylon, PPE, PEEK) can be attached to the outside of the sleeve 100 for rigidity or insulation.

Figure 3:
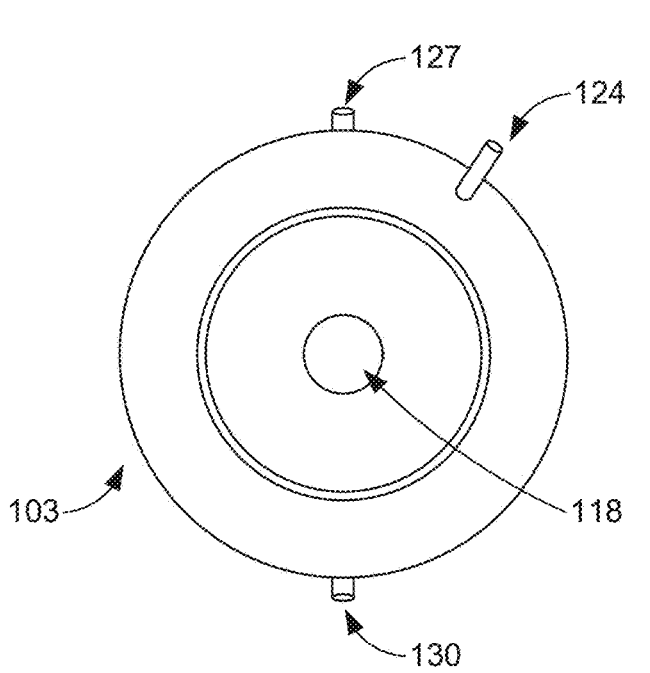
FIG. 3 illustrates a top-down view of an exemplary sleeve, in accordance with the disclosed technology.

Referring now to FIG. 3, a top-down view of an exemplary sleeve 100 is shown. The proximal opening 118 can be centrally located on the top side of the drill coupler 103 (e.g., the proximal opening 118 can be located in the center of the top side of the drill coupler 103). The proximal opening 118 forms a continuous drill channel 120 with the distal opening 121 (e.g., the proximal opening 118 at the top of the drill coupler 103 and the distal opening 121 at the bottom of the drill body 106 form a continuous channel). A surgical drill can be inserted into the proximal opening 118 and attached to the drill coupler 103. The suction connection point 124 can be adjacent to the proximal opening 118. The fluid inlet connection point 127 and the fluid outlet connection point 130 can be located on opposite sides of the drill coupler 103.

Figure 4:
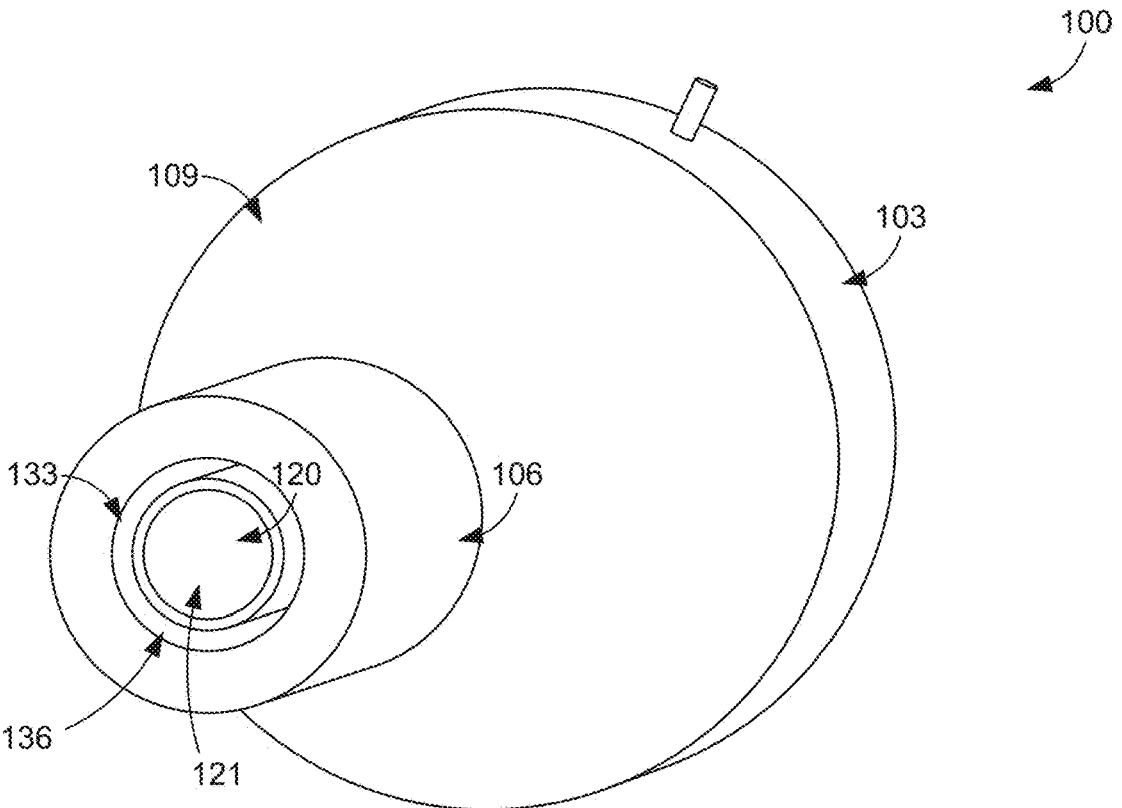
FIG. 4 illustrates a bottom-up view of an exemplary sleeve, in accordance with the disclosed technology.

Referring now to FIG. 4, a bottom-up view of an exemplary sleeve 100 is shown. The distal opening 121 can be centrally located on the bottom side of the sleeve body 106 (e.g., the distal opening 121 can be located in the center of the bottom of the sleeve body 106). The sleeve body 106 can include a suction inlet 133. The suction inlet 133 can be the opening at the bottom of the suction channel 136. The suction channel 136 can be a circular concentric channel located around the drill channel 120 (e.g., the suction channel 136 can be a concentric channel around the outside of the drill channel 120). The suction inlet 133 can be a concentric opening around the distal opening 121 (e.g., the distal opening 121 can be a circular opening and the suction inlet 133 can be a concentric opening).

Figure 5:
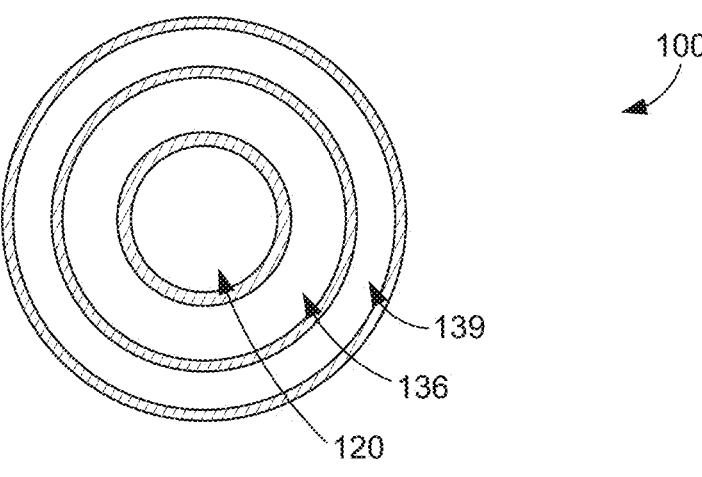
FIG. 5 illustrates a top cross-sectional view of an exemplary sleeve body, in accordance with the disclosed technology.

Referring now to FIG. 5, a top cross-sectional view of an exemplary sleeve 100 is shown. The sleeve 100 can include a drill channel 120, a suction channel 136, and cooling channel 139. The drill channel 120 can be a generally circular channel located in the center of the sleeve 100 (e.g., the drill channel 120 can have a generally circular cross-sectional shape). The suction channel 136 and the cooling channel 139 can be circular concentric channels located on the outside of the drill channel 120 (e.g., the suction channel 136 and cooling channel 139 can have a generally concentric cross-sectional shape). The cooling channel 139 can be the outermost channel and the suction channel 136 can be located between cooling channel 139 and the drill channel

11

120. Alternatively, the suction channel 136 can be the outermost channel and the cooling channel 139 can be located between the suction channel 136 and the drill channel 120.

Figure 6:
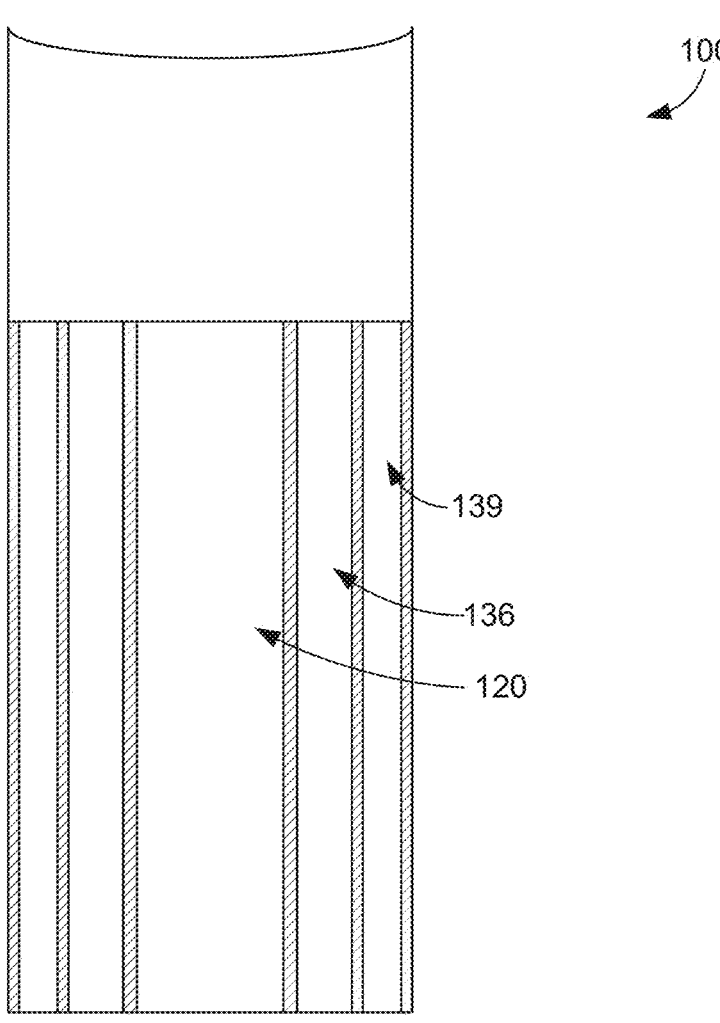
FIG. 6 illustrates a side cross-sectional view of an exemplary sleeve body, in accordance with the disclosed technology.

Referring now to FIG. 6, a side cross-sectional view of an exemplary sleeve 100 is shown. As discussed with reference to FIG. 5, the drill channel 120 can be the centermost channel in the sleeve 100, the cooling channel 139 can be the outermost channel, and the suction channel 136 can be located in between the drill channel 120 and cooling channel 139. The suction channel 136 and the cooling channel 139 can have a generally concentric cross-sectional shape and be located outside the drill channel. The drill channel 120 can be any width sufficient to fit a surgical drill. The width of the drill channel 120 can vary depending on the type of surgical drill used and the intended procedure. The width of the suction channel 136 can vary depending on the intended procedure (e.g., the suction channel 136 can be sufficient width to remove debris from the surgical site). The width of the cooling channel 139 can vary depending on the necessary volume of cooling fluid to remove heat from the sleeve 100.

Figure 7:
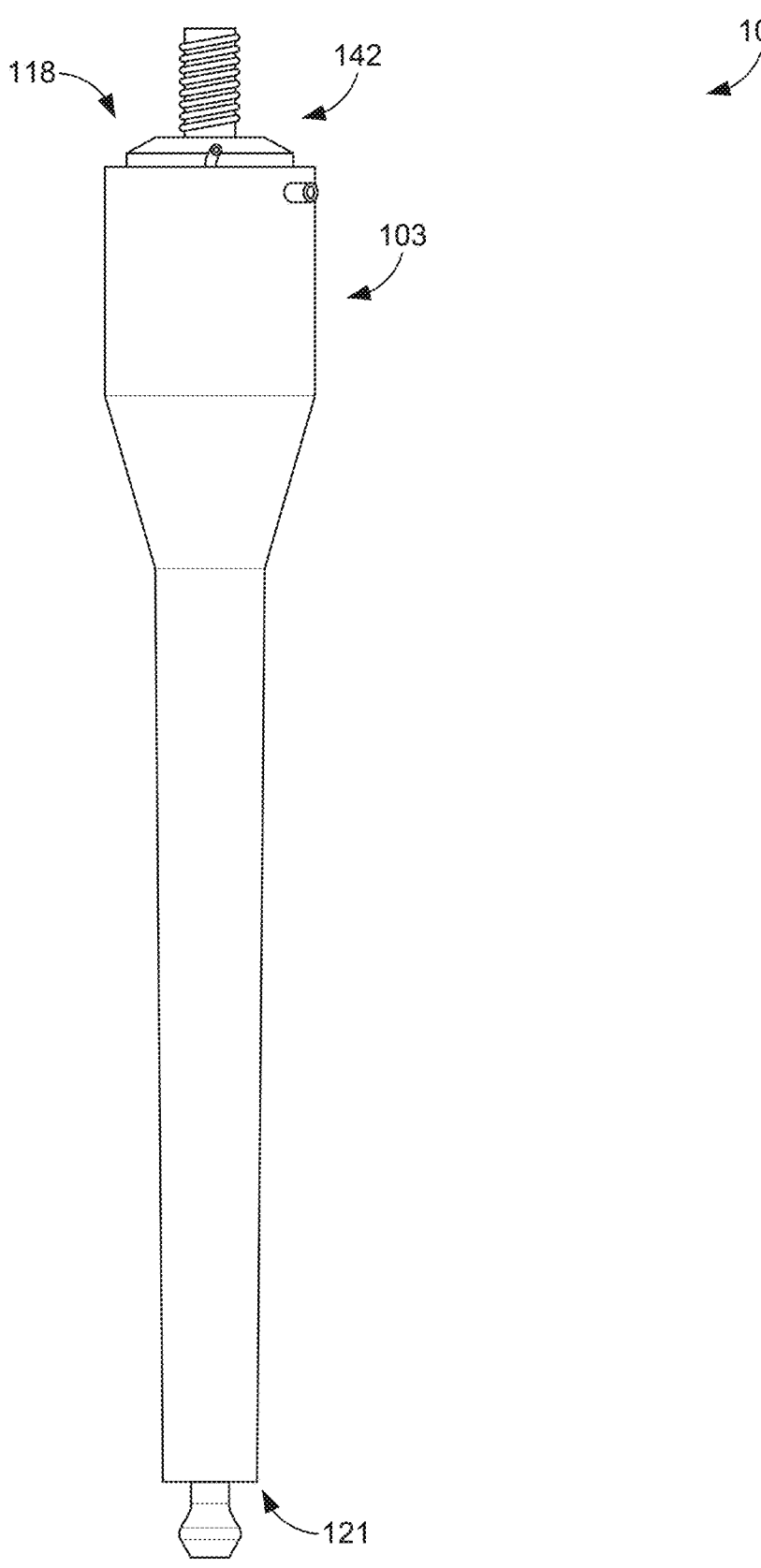
FIG. 7 illustrates a surgical drill inserted into an exemplary sleeve, in accordance with the disclosed technology.

Referring now to FIG. 7, a surgical drill 142 is shown inserted into an exemplary sleeve 100. A surgical drill 142 can be inserted into the proximal opening 118. The drill bit of the surgical drill 142 can pass through the drill channel 120 and exit through the distal opening 121. The surgical drill 142 can be attached (e.g., secured or connected) to the drill coupler 103 such that the sleeve 100 remains attached to the surgical drill 142 throughout a procedure. The surgical drill 142 can be detached from the drill coupler 103.

Figure 8:
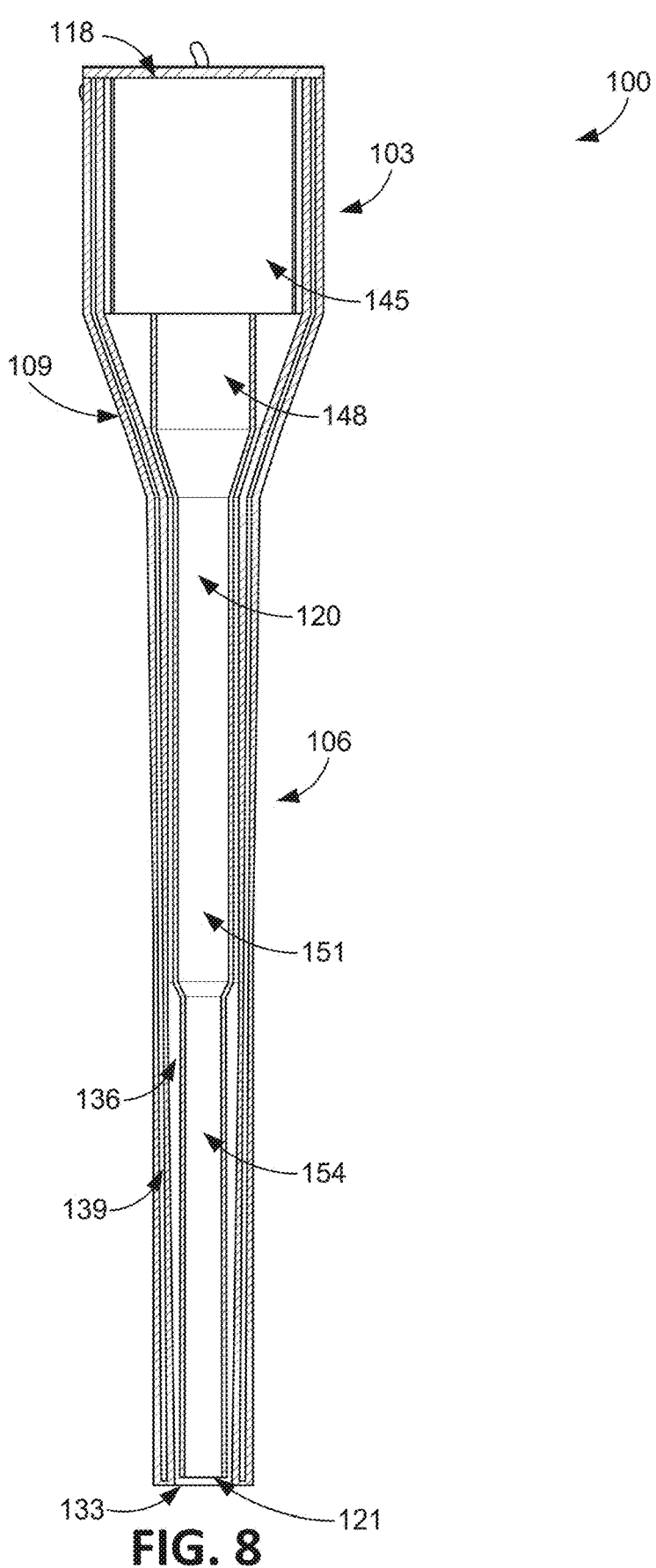
FIG. 8 illustrates a side cross-sectional view of an exemplary sleeve, in accordance with the disclosed technology.

Referring now to FIG. 8, a side cross-sectional view of an exemplary sleeve 100 is shown. The drill channel 120 can be located in the center of the sleeve 100. The drill channel 120 can begin with the proximal opening 118 at the top of the drill coupler 103 and extend to the distal opening 121 at the bottom of the sleeve body 106. The width of the drill channel 120 can be incrementally reduced so that a surgical drill can be interference fitted with the sleeve 100 (e.g., the sleeve 100 can be friction fitted around a surgical drill such that the sleeve 100 remains connected to the drill during a procedure).

The drill channel 120 can include an upper portion 145 located within the drill coupler 103. The upper portion 145 located within the drill coupler 103 can have the largest width compared the rest of the drill channel 120. The drill channel 120 can include an intermediary portion 148 within the intermediary section 109 of the sleeve 100. The intermediary portion 148 can have a width less than the width of the upper portion 145. The width of the intermediary portion 148 can decrease down the length of the intermediary section 109. The drill channel 120 can include a first sleeve portion 151 within the sleeve body 106. The first sleeve portion 151 can be a length less than the length of the sleeve body 106 (e.g., half the length of the sleeve body 106) and be located in the top half of the sleeve body 106. The width of the first sleeve portion 151 can be less than the width of the intermediary portion 148. The drill channel 120 can include a second sleeve portion 154 within the sleeve body 106. The second sleeve portion 154 can be a length less than the length of the sleeve body 106 (e.g., half the length of the sleeve body 106) and be located in the bottom half of the sleeve body 106. The width of the second sleeve portion 154 can be less than the width of the first sleeve portion 151.

The suction channel 136 can have a generally circular concentric cross-sectional shape and be located outside of and adjacent to the drill channel 120 (e.g., the suction channel 136 can be a concentric channel around the outside of the drill channel 120). The suction channel 136 can begin at the top of the drill coupler 103 and extend straight down the length of the sleeve 100 to the bottom of the sleeve body 106. The suction channel 136 can terminate at the suction inlet 133 at the bottom of the sleeve body 106. The cooling channel 139 can have a generally circular concentric cross-sectional shape and be located outside of and adjacent to the suction channel 136 (e.g., the cooling channel 139 can be a concentric channel around the outside of the suction channel 136). The cooling channel 139 can begin at the top of the drill coupler 103 and extend straight down the length of the sleeve 100 to the bottom of the sleeve body 106.

Figure 9:
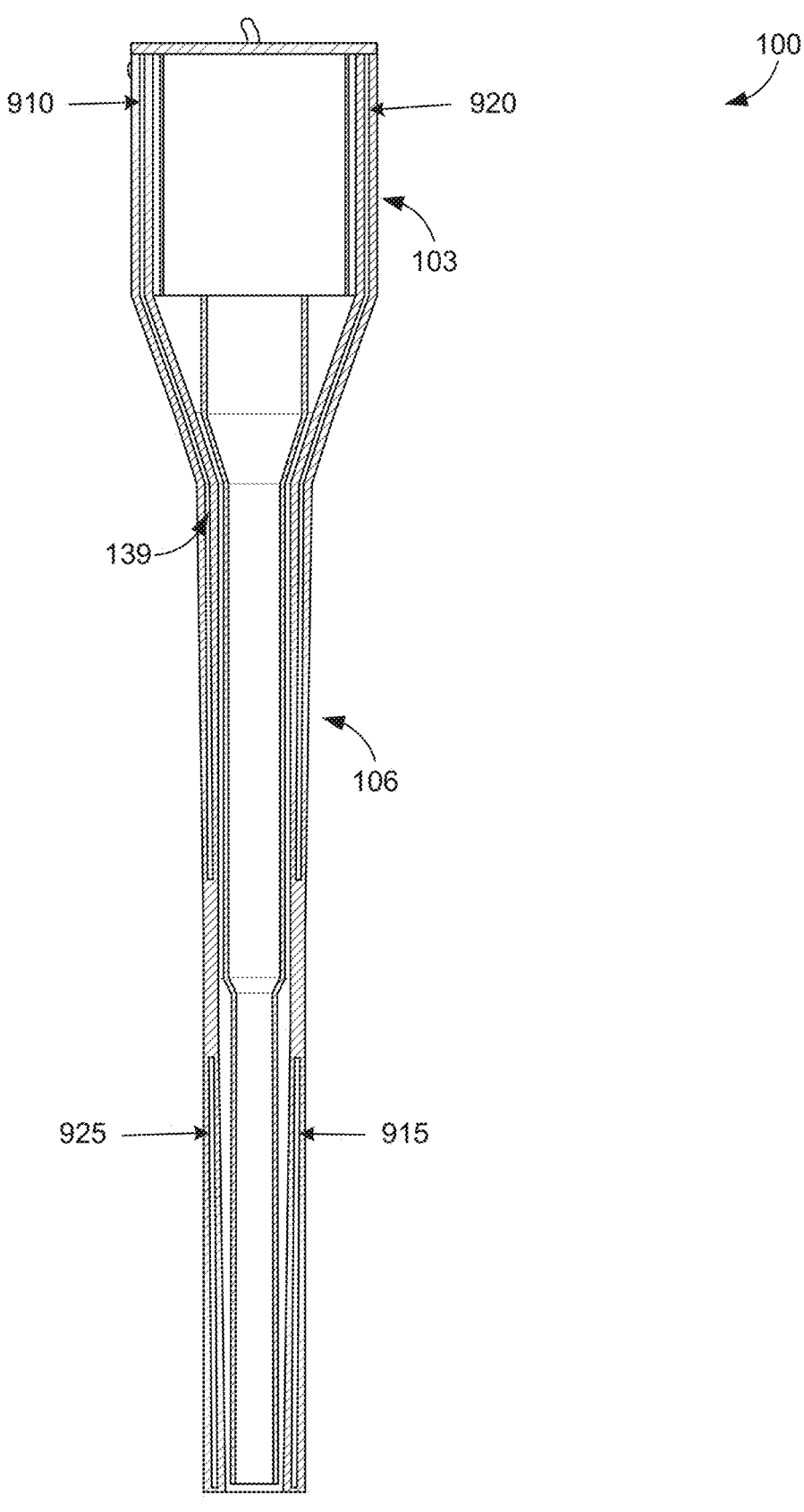
FIG. 9 illustrates a side cross-sectional view of an exemplary sleeve, in accordance with the disclosed technology.

Referring now to FIG. 9, an XY plane cross-sectional view of an exemplary sleeve 100 is shown. Alternatively or in addition, the cooling channel 139 can include a loop channel with an upper inlet portion 910 and an upper outlet portion 920. Both the upper inlet portion 910 and the upper outlet portion 920 of the cooling channel 139 can each have a half-circular concentric cross-sectional shape (e.g., the upper inlet portion 910 can be one half of a concentric circular channel and the upper outlet portion 920 can be the other half of the circular channel). The upper inlet portion 910 can fluidly connect to the fluid inlet connection point 127 and longitudinally extend along one side of the sleeve 100. At some point along the length of the sleeve body 106 (e.g., halfway down the sleeve body 106), the upper inlet portion 910 can cross over the width of the sleeve body 106 to the opposite side of the sleeve 100 (e.g., as shown and described in more detail with respect to FIG. 10), such that a refrigerant can flow from the upper inlet portion 910 to a lower inlet portion 915. After crossing over the width of the sleeve body 106, the lower inlet portion 915 can extend to the bottom of the sleeve body 106. The lower inlet portion 915 can fluidly connect to a lower outlet portion 925 (e.g., the side of the cooling channel 139 located on the opposite side of the sleeve 100 from the lower inlet portion 915) at the bottom of the sleeve body 106. The lower outlet portion 925 can longitudinally extend along one side of the sleeve 100. At some point along the length of the sleeve body 106 (e.g., halfway up the sleeve body 106), the lower outlet portion 925 can cross over the width of the sleeve body 106 to the opposite side of the sleeve 100. After crossing over the width of the sleeve body 106, the upper outlet portion 920 can longitudinally extend along the sleeve 100 to or near the top of the drill coupler 103 and can fluidly connect with the fluid outlet connection point 130.

Figure 10:
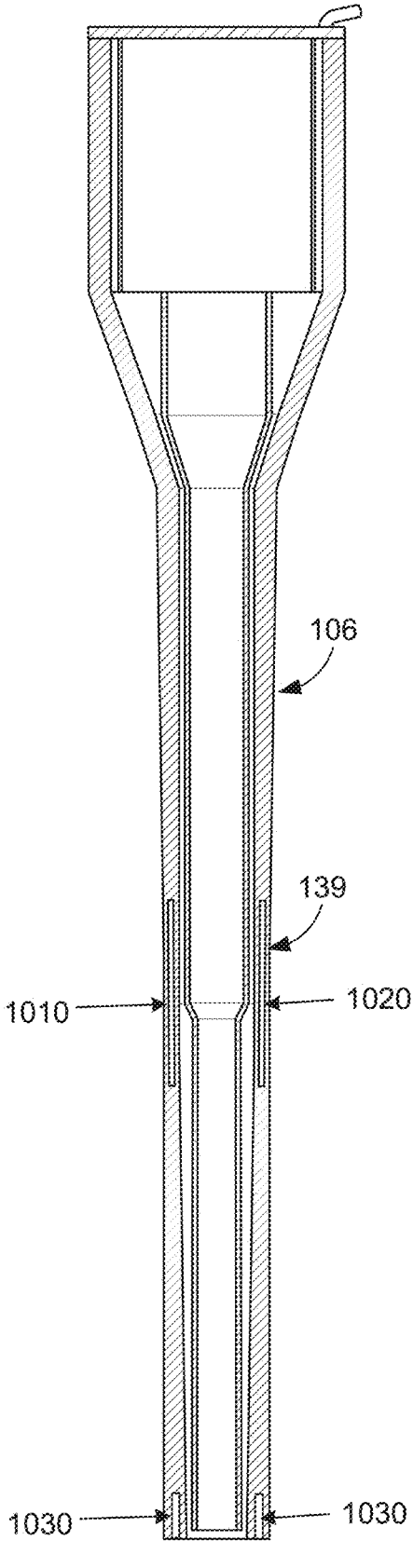
FIG. 10 illustrates a side cross-sectional view of an exemplary sleeve, in accordance with the disclosed technology.

Referring now FIG. 10 and continuing with the cooling sleeve 100 described in FIG. 9, an YZ plane cross-sectional view of an exemplary sleeve is shown. The cooling channel 139 can include an inlet crossover portion 1010 and an outlet crossover portion 1020. The inlet crossover portion 1010 can be located at some point along the length of the sleeve body 106 (e.g., halfway down the sleeve body 106). The inlet crossover portion 1010 can provide a flow path for refrigerant to cross over the width of the sleeve body 106 from the upper inlet portion 910 to the lower inlet portion 915 on the opposite side of the sleeve 100. The outlet crossover portion 1020 can be located at some point along the length of the sleeve body 106 (e.g., halfway up the sleeve body 106). The outlet crossover portion 1020 can provide a flow path for refrigerant to cross over the width of the sleeve body 106 from the lower outlet portion 925 to the upper outlet portion 920 on the opposite side of the sleeve 100. The cooling channel 139 can include a lower crossover portion 1030. The lower crossover portion 1030 can be located at the bottom of the sleeve body 106. The lower crossover portion 1030 can provide a flow path for refrigerant to cross over the width of the sleeve body 106 from the lower inlet portion 915 to the lower outlet portion 925.

By "crossing over the width of the sleeve body 106," it is meant that the flow channel defined by the upper inlet portion 910 flows along a circumferential flow path (e.g., at the inlet crossover portion 1010) to the lower inlet portion 915, which is located on the opposite side of the sleeve 100 from the upper inlet portion 910, and likewise, the flow channel defined by the lower outlet portion 925 flows along a circumferential flow path (e.g., at the outlet crossover portion 1020) to the upper outlet portion 920, which is located on the opposite side of the sleeve 100 from the lower outlet portion 925. The flow channel defined by the lower crossover portion 1030 flows along a circumferential flow path connecting the lower inlet portion 915 to the lower outlet portion 925.

Further, the inlet crossover portion 1010, the outlet crossover portion 1020, and the lower crossover portion 1030 are shown in the cross-sectional view of FIG. 10 as having tops and bottoms that are substantially perpendicular to the outer surface of the sleeve 100 and/or the outer or inner walls of the cooling channel 139, but the technology is not so limited. For example, the inlet crossover portion 1010 and/or the outlet crossover portion 1020 and/or the lower crossover portion 1030 can have a generally helical (e.g., semi-helical) flow path, such that the top and/or bottom of the inlet crossover portion 1010, the outlet crossover portion 1020, and/or the lower crossover portion 1030 can be sloped downwardly along the circumference of the cooling channel 139.

Figure 11:
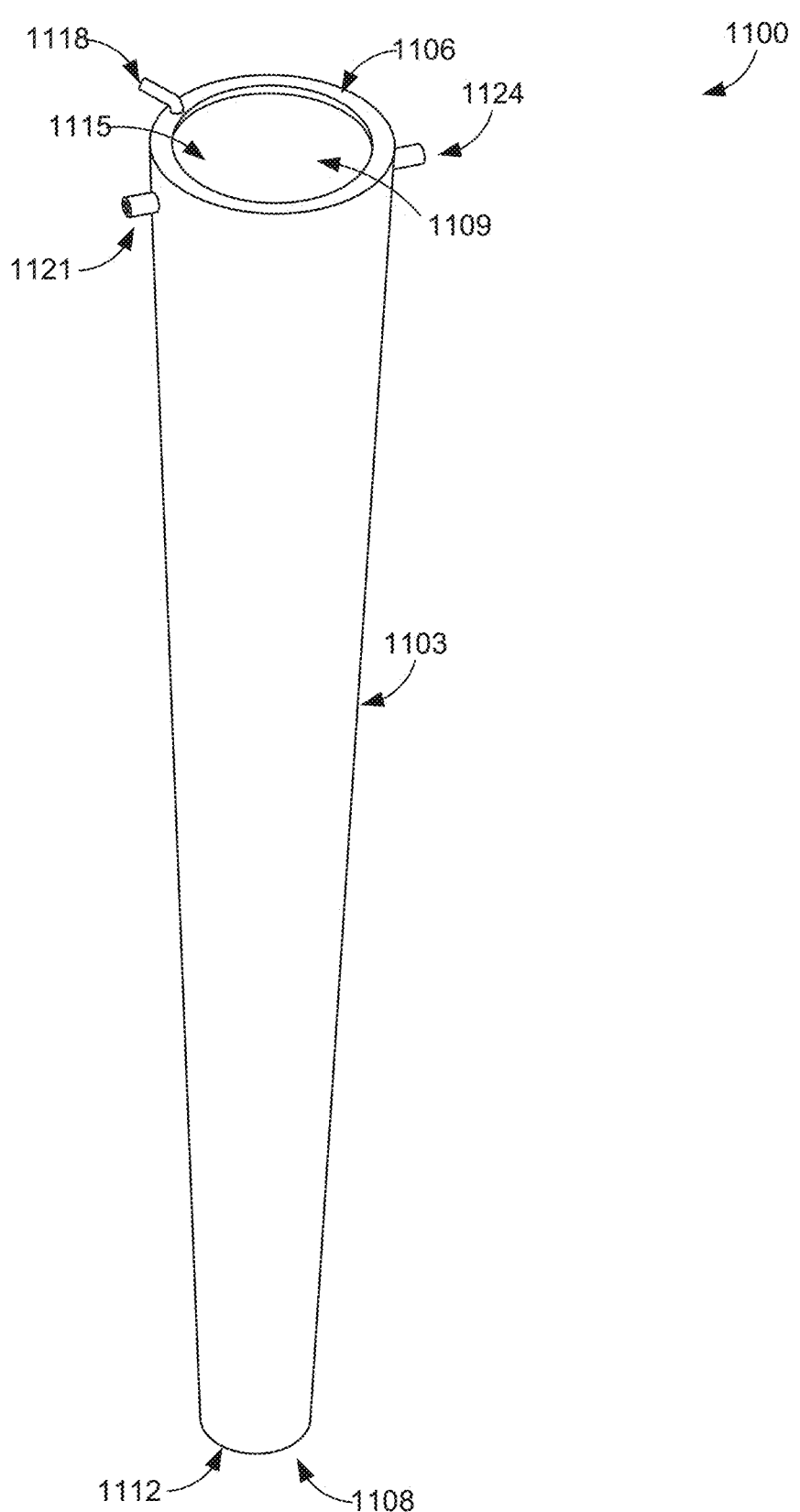
FIG. 11 illustrates a perspective view of an exemplary sleeve, in accordance with the disclosed technology.

Referring now to FIG. 11, a perspective view of an exemplary sleeve is shown 1100. The sleeve 1100 can include a sleeve body 1103. The sleeve body 1103 can have a tapered cylinder shape. The diameter at the top 1106 of the sleeve body 1103 can be greater than the diameter at the bottom 1108 of the sleeve body. The diameter at the bottom 1108 of the sleeve body 1103 can be 3 millimeters or less.

A proximal opening 1109 can be located at the top 1106 of the sleeve body 1103. The proximal opening 1109 can be an opening at the top 1106 of the sleeve body 1103 for a surgical drill to be inserted into the sleeve 1100. The proximal opening 1109 can form a drill channel that can extend the length of the sleeve body 1103. A surgical drill can be secured to the sleeve 1100 either by the proximal opening 1109 or the sleeve body 1103 such that the sleeve 1100 remains attached to the surgical drill throughout a procedure. The surgical drill can be detached from the sleeve 1100.

A distal opening 1112 can be located at the end of the sleeve body 1103. The distal opening 1112 can form a continuous drill channel 1115 with the proximal opening 1109 (e.g., the distal opening 1112 can be one end of a drill channel 1115 formed with the proximal opening 1109). Once a surgical drill has been inserted into the proximal opening 1109 and through the drill channel 1115, the drill bit of the surgical drill can exit the distal opening 1112 such that drill bit can be used in a procedure.

A suction connection point 1118 can be located at the top of the sleeve body 1103. The suction connection point 1118 can be provide suction (e.g., a pressure differential) at a surgical site via a suction device (e.g., a medical device able to provide suction during a procedure). The suction connection point 1118 can be used to connect a hose or tube from a suction device to the sleeve 1100. The suction connection point 1118 can be any appropriate connection point for connecting a tube, hose, or suction device to the sleeve (e.g., attaching or securing a tube, hose, or suction device to the sleeve 1100 such that the tube, hose, or suction device can remain attached or secured to the sleeve 1100 throughout a procedure). The suction provided by a suction device connected to the suction connection point 1118 via a hose or tube can be used to remove bone, mucus, saliva, or other debris from a surgical site. The suction connection point 1118 can be connected to a suction channel.

A fluid inlet connection point 1121 and a fluid outlet connection point 1124 can be located at the top of the sleeve body 1103. The fluid inlet connection point 1121 can provide cooling fluid to the sleeve 1103. The cooling fluid can be or include any refrigerant or fluid (e.g., gas or fluid) appropriate for medical use that can remove heat from the sleeve 1103 (e.g., nitrous oxide, Freon, liquid helium). Cooling fluid can enter the sleeve 1103 through the fluid inlet connection point 1121 and exit the sleeve through the fluid outlet connection point 1124. Both the fluid inlet connection point 1121 and the fluid outlet connection point 1124 can be used to connect a hose or tube from a gas source (e.g., a gas tank, gas supply line) to the sleeve 1100. Both the fluid inlet connection point 1121 and the fluid outlet connection point 1124 can be any appropriate connection point for connecting a tube or hose (e.g., attaching or securing a tube or hose to the sleeve 1100 such that the tube or hose can remain attached or secured to the sleeve 1100 throughout a procedure). Both the fluid inlet connection point 1121 and the fluid outlet connection point 1124 can be connected to a cooling channel.

Figure 12:
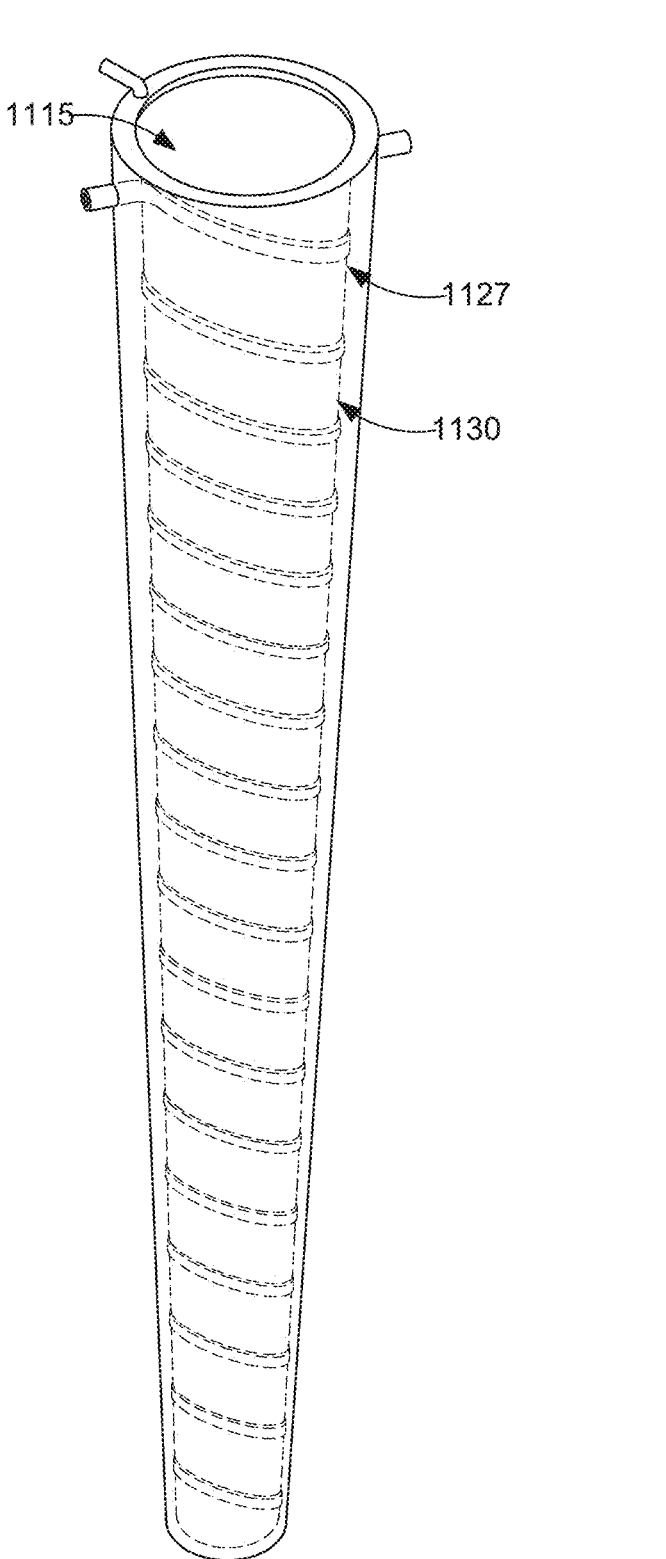
FIG. 12 illustrates a transparent side view of an exemplary sleeve, in accordance with the disclosed technology.

As will be understood, FIGS. 12-19 can illustrate various example configurations of the cooling channel. The disclosed technology includes various combinations of the various aspects and/or configurations disclosed herein, even if a given combination is not explicitly illustrated or described herein. For example, one or more of the example configurations shown and described with respect to FIGS. 12-19 can include some or all of the elements shown and described with respect to FIG. 11. Referring now to FIG. 12, a transparent side view of an exemplary sleeve 1100 is shown. The cooling channel 1127 can have a generally helical shape. The helical cooling channel 1127 can wrap around the drill channel 1115 in the center of the sleeve 1100. Alternatively or in addition, the helix shaped cooling channel 1127 can wrap around a circular concentric suction channel 1130. Alternatively, the cooling channel 1127 can have a generally double-helical shape (e.g., one side of the double helix can guide an inflow of the cooling fluid and the other side of the double helix can guide an outflow of the cooling fluid).

Figure 13:
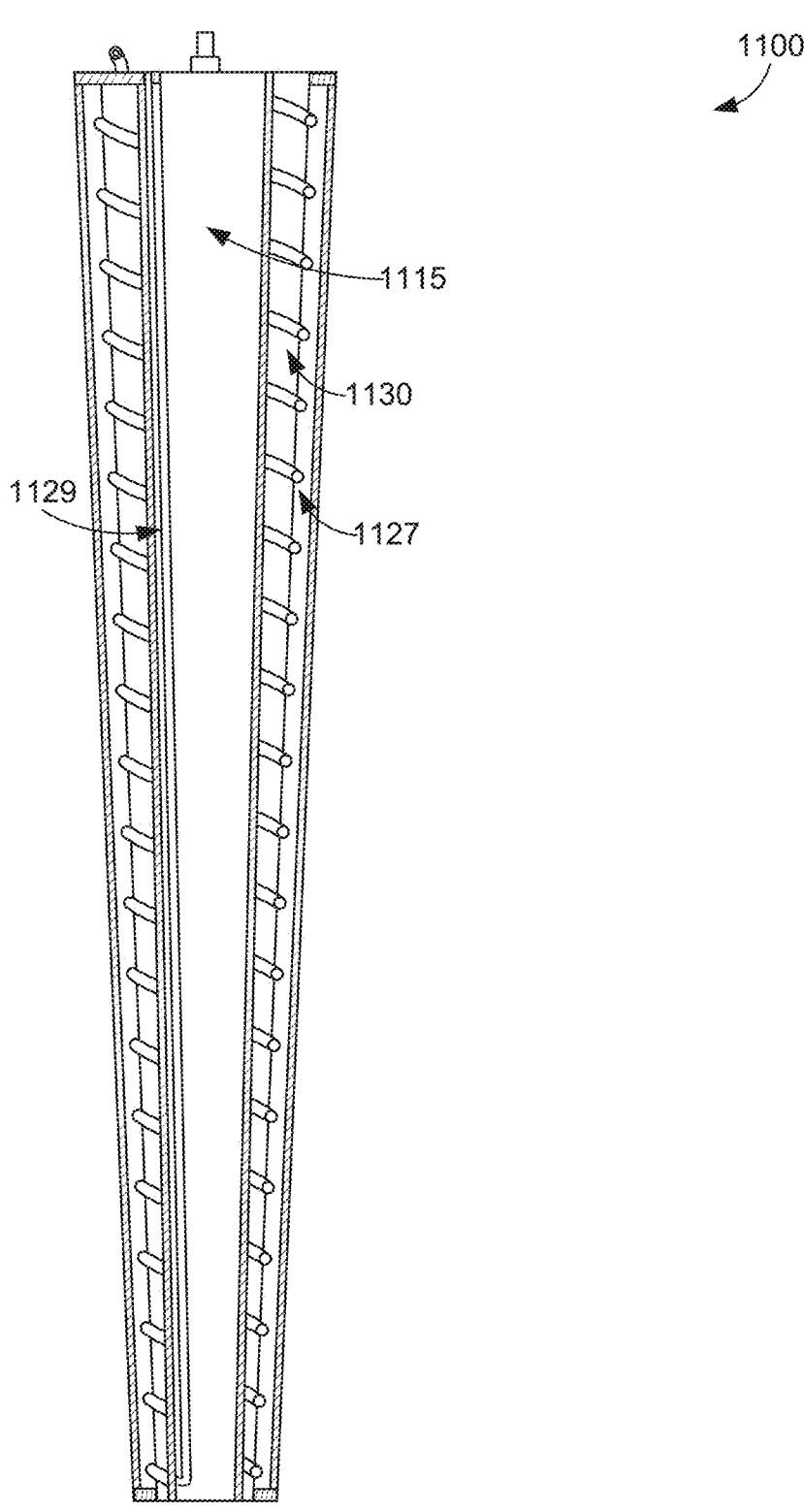
FIG. 13 illustrates a side cross-sectional view of an exemplary sleeve, in accordance with the disclosed technology.

Referring now to FIG. 13, a side cross-sectional view of an exemplary sleeve 1100 is shown. The sleeve 1100 can include the drill channel 1115, the suction channel 1130, and the cooling channel 1127. A circular drill channel 1115 can be located at the center of the sleeve 1100. A helical cooling channel 1127 can wrap around the drill channel 1115. The helical cooling channel 1127 can include a longitudinal portion 1129 that can be in fluid connection with the helical cooling channel 1127 at the bottom of the sleeve 1100. The longitudinal portion 1129 can extend from the bottom of the sleeve 1100 to the top of the sleeve 1100 and be in fluid connection with the fluid outlet connection point. The longitudinal portion 1129 can be located radially internal to the helical cooling channel 1127 and the suction channel 1130. A circular concentric suction channel 1130 can be located outside of both the drill channel 1115 and the helical gas channel 1127. Alternatively or in addition, a concentric suction channel 1130 can be located outside of the drill channel 1115 and the helical gas cooling channel 1127 can wrap around the suction channel 1130.

Figure 14:
FIG. 14 illustrates a top cross-sectional view of an exemplary sleeve, in accordance with the disclosed technology.
Figure 14:
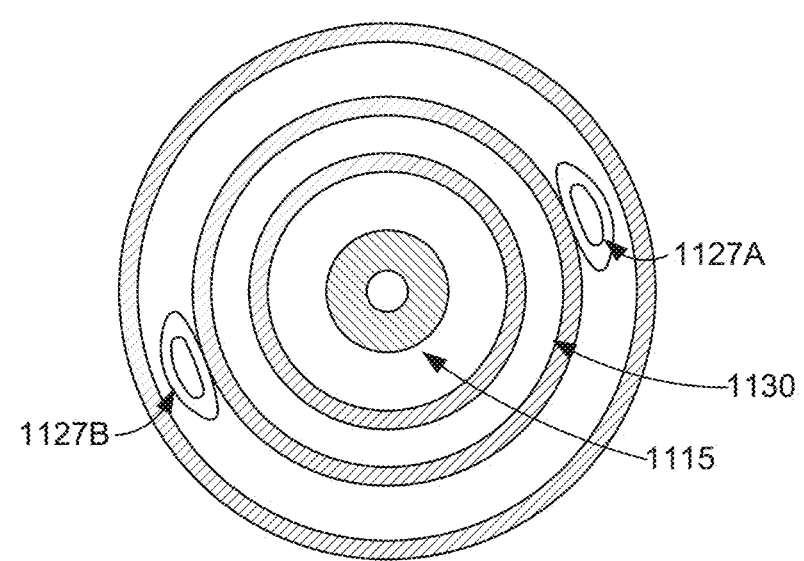

Referring now to FIG. 14, a top cross-sectional view of an exemplary sleeve 1100 is shown. A surgical drill can be inserted into the circular drill channel 1115 located at the center of the sleeve 1100. The circular concentric suction channel 1130 can be located outside of and adjacent to the drill channel 1115 (e.g., the suction channel 1130 can be a concentric channel around the outside of the drill channel 1115). The cooling channel 1127 can be or have a helical or double-helical shape and wrap around the suction channel 1130. The cooling channel 1127 can include both an inlet end 1127A and outflow end 1127B located across from each other on opposite sides of the sleeve 1100. The inflow end 1127A can fluidly connect to the fluid inlet connection point to allow cooling fluid to enter the sleeve 1100. The inflow end 1127A can fluidly connect with the outflow end 1127B to allow cooling fluid to flow throughout the length of the sleeve 1100. The outflow end 1127B can connect to the fluid outlet connection point to allow cooling fluid to exit the sleeve 1100.

Figure 15:
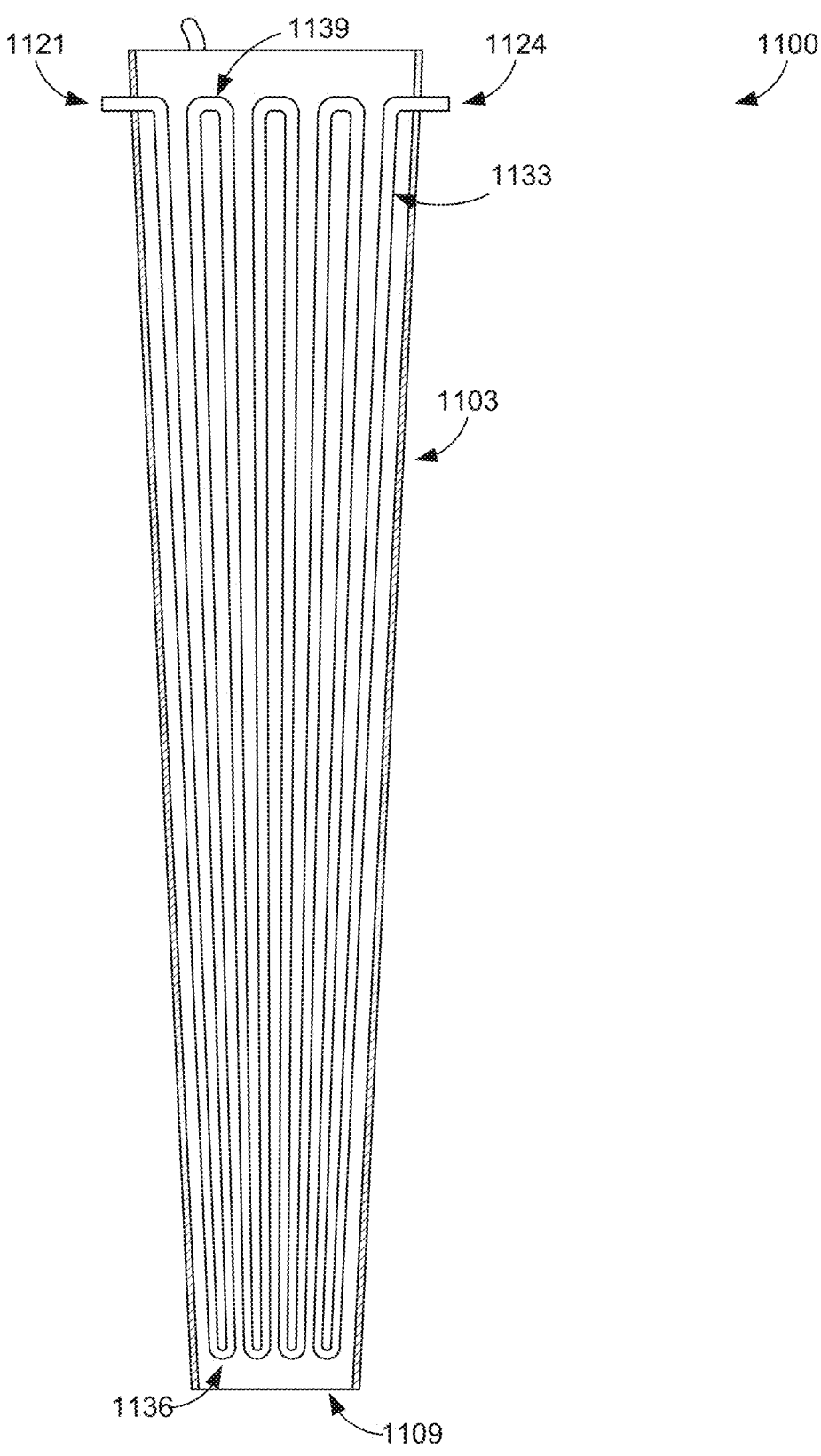
FIG. 15 illustrates a transparent side view of an exemplary sleeve, in accordance with the disclosed technology.

Referring now to FIG. 15, a transparent side view of an exemplary sleeve 1100 is shown. The cooling channel loop 1133 can include multiple loops extending the length of the sleeve 1100. A cooling channel loop 1133 can start at the fluid inlet connection point 1121 (e.g., be in fluid communication with the fluid inlet connection point 1121) and extending axially down the length of the sleeve 1100 towards the sleeve body 1103. At the bottom of or proximate to the bottom 1108 of the sleeve body 1103, the cooling channel loop 1133 can include a bend 1136 and can reverse directions (e.g., turn approximately 180°) and extend axially up the length of the sleeve body 1103. At the top of or proximate to the top of the sleeve body 1103, the cooling channel loop 1133 can include a bend 1139 and can reverse directions (e.g., turn approximately 180°) and extend axially down the length of the sleeve body 1103. This pattern can be repeated any number of times to provide a zig-zagging flow path up and down the length of the sleeve 1100. The cooling channel loop 1133 can eventually connect with, or otherwise be in fluid communication with, the fluid outlet connection point 1124.

Figure 16:
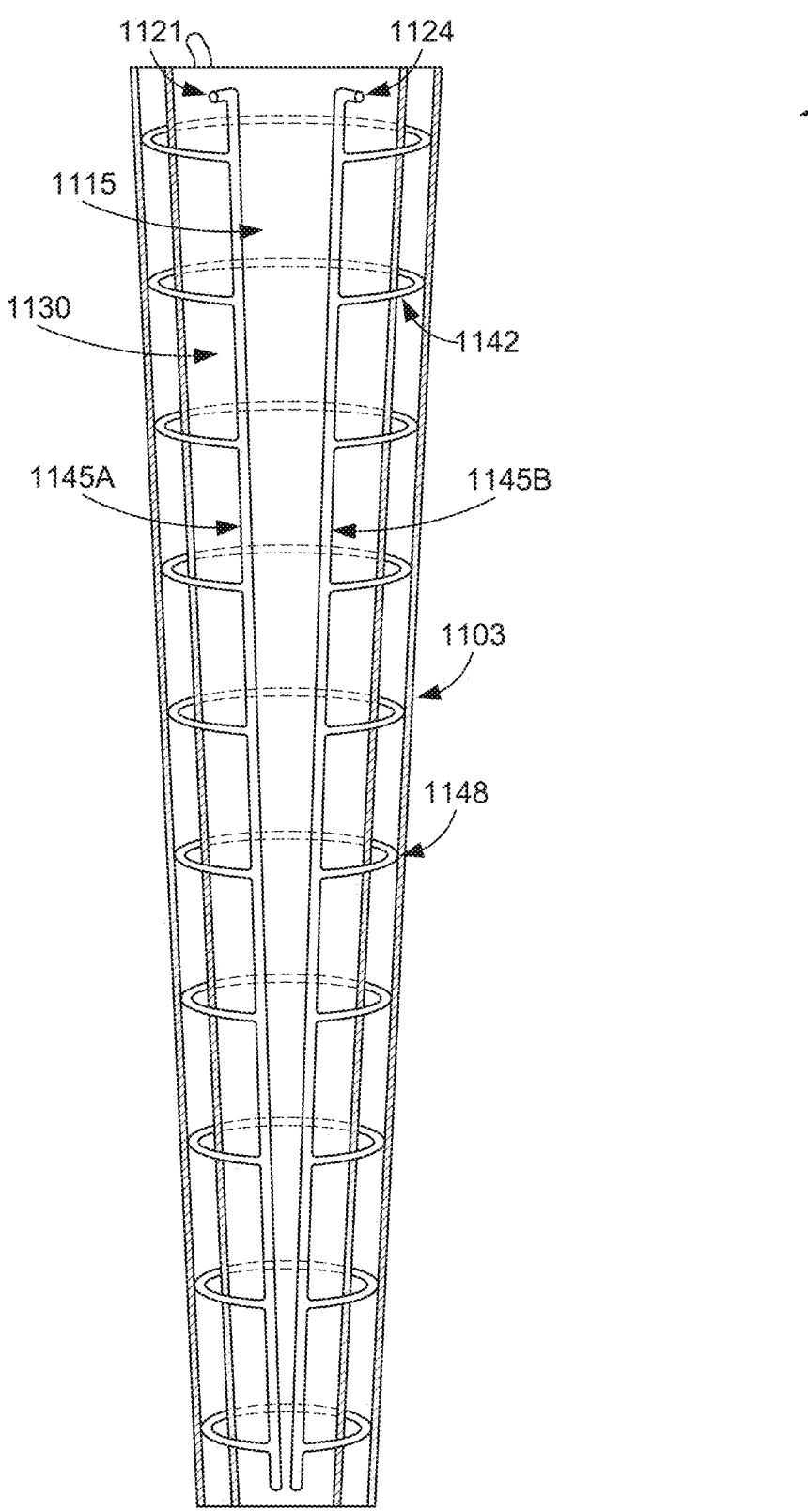
FIG. 16 illustrates a transparent side view of an exemplary sleeve, in accordance with the disclosed technology.

Referring now to FIG. 16, a transparent side view of an exemplary sleeve is shown. The cooling channel 1142 can include two axially-extending flow paths 1145A and 1145B, which can each extend in a generally axial direction along a portion of the length of the sleeve body 1103. One axially-extending flow path 1145A can connect to, or otherwise be in fluid communication with, the fluid inlet connection point 1121, and the other axially-extending flow path 1145B can connect to, or otherwise be in fluid communication with, the fluid outlet connection point 1124. The axially-extending flow paths 1145A and 1145B can be approximately parallel. Alternatively, the axially-extending flow paths 1145A and 1145B can be angled with respect to one another. The axially-extending flow paths 1145A and 1145B can include multiple loops 1148 that extend in a generally circumferential direction (e.g., wrap or arc around the drill channel 1115 to fluidly connect the two axially-extending flow paths 1145A and 1145B). For example, the multiple loops 1148 can wrap around the circular concentric suction channel 1130.

Figure 17:
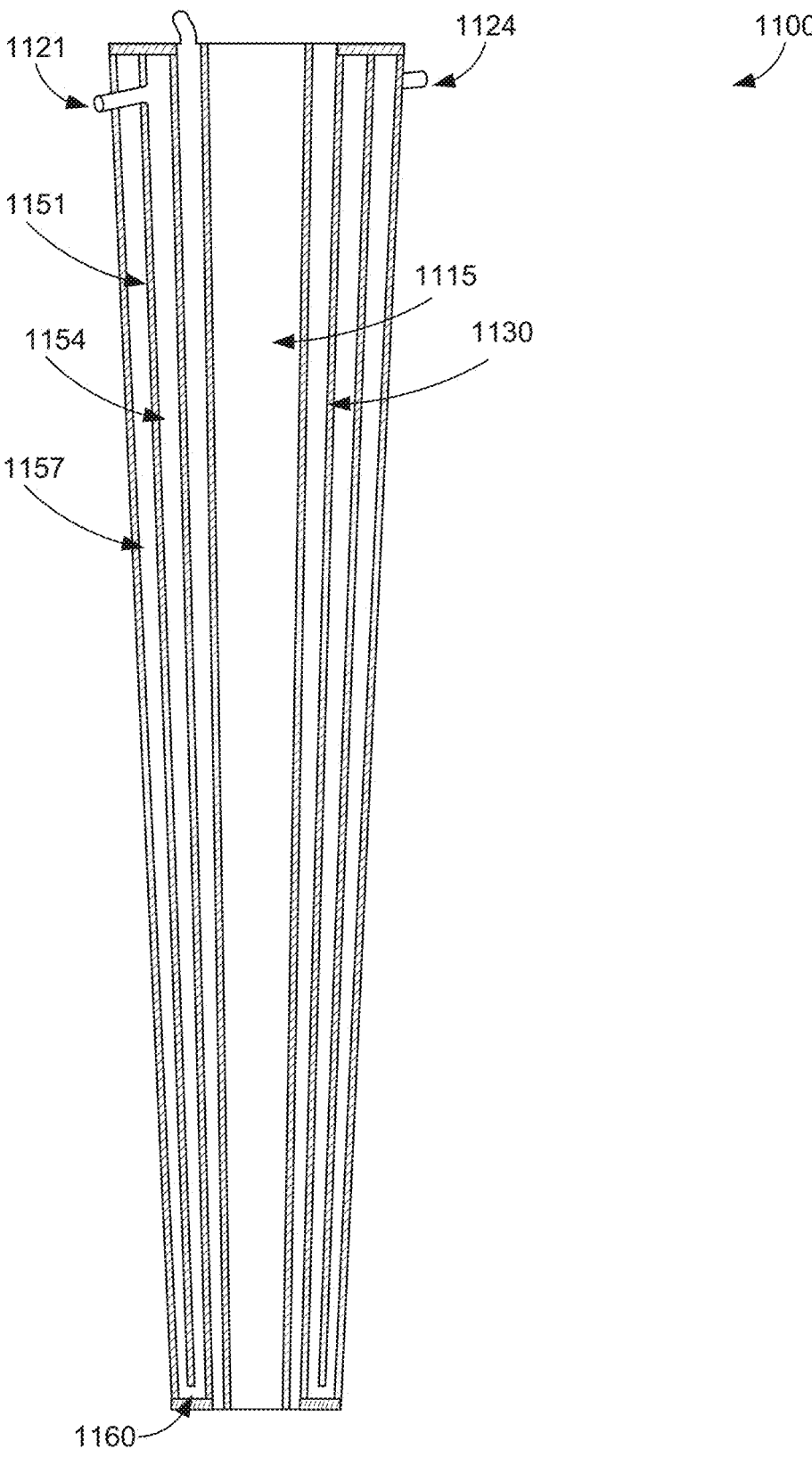
FIG. 17 illustrates a side cross-sectional view of an exemplary sleeve, in accordance with the disclosed technology.

Referring now to FIG. 17, a cross-sectional side view of an exemplary sleeve 1100 is shown. The circular drill channel 1115 can be located at the center of the sleeve 1100. The circular concentric suction channel 1130 can be located outside of and adjacent to the center drill channel 1115 (e.g., the suction channel 1130 can be a concentric channel around the outside of the drill channel 1115). The cooling channel 1151 can include an inner channel 1154 and outer channel 1157. The outer channel 1157 can be located outside of, and adjacent to, the inner channel 1154. The inner channel 1154 and outer channel 1157 can be concentric. The inner channel 1154 and the outer channel 1157 can fluidly connect at or near the bottom of the sleeve 1100. For example, a wall separating the inner channel from the outer channel can terminate to provide a passage 1160 between the inner channel 1154 and the outer channel 1157. The inner channel 1154 can be connected to the fluid inlet connection point 1121, and the outer channel 1157 can be connected to the fluid outlet connection point 1124. Alternatively, the outer channel 1157 can be connected to the fluid inlet connection point 1121, and the inner channel 1154 can be connected to the fluid outlet connection point 1124.

Figure 18:
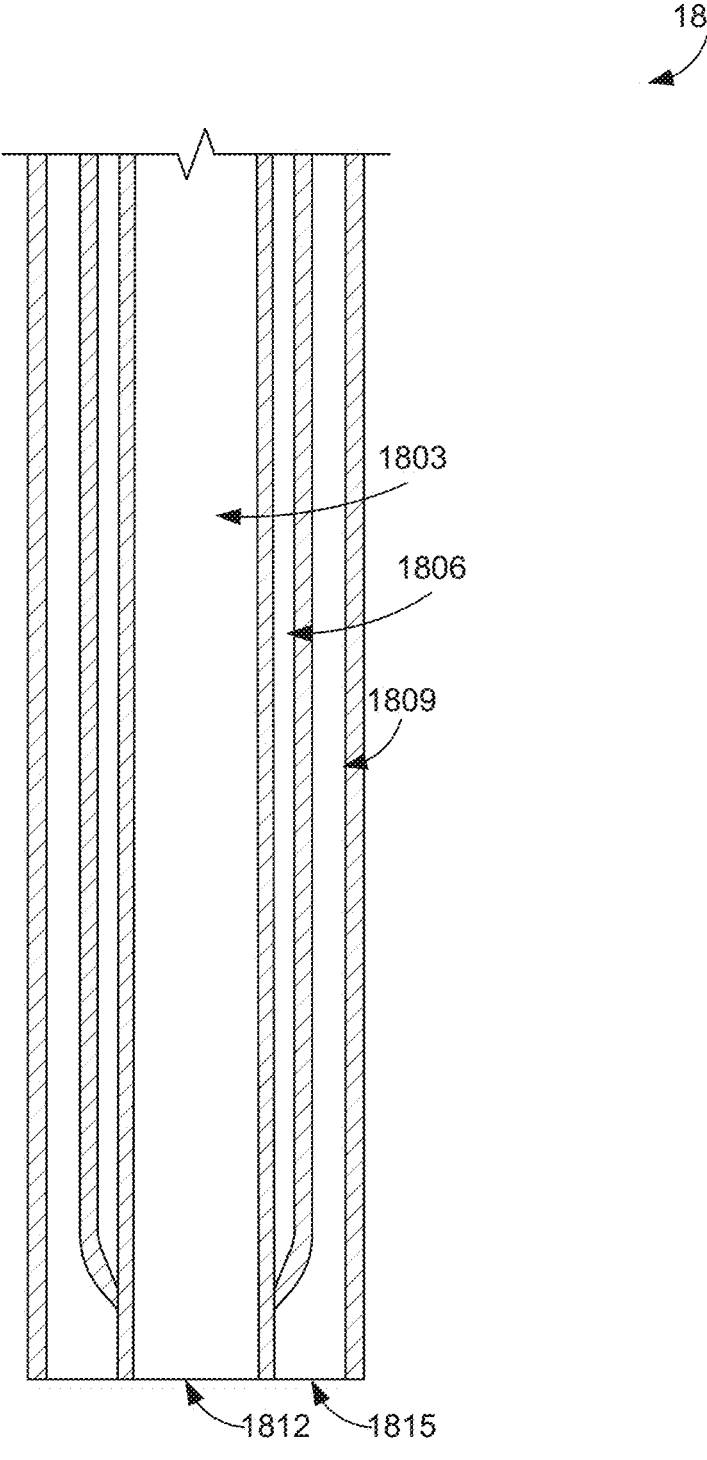
FIG. 18 illustrates a side cross-sectional view of an exemplary sleeve, in accordance with the disclosed technology.

Referring now to FIG. 18, a side cross-sectional view of an exemplary sleeve 1800 is shown. The circular drill channel 1803 can be located at the center of the sleeve 1800. The cooling channel 1806 can be a circular concentric channel located outside of and adjacent to the drill channel 1803 (e.g., the cooling channel 1806 can be a concentric channel around the outside of the drill channel 1803). The suction channel 1809 can be a circular concentric channel located outside of and adjacent to the cooling channel 1806 (e.g., the suction channel 1809 can be a concentric channel around the outside of the cooling channel 1806). The cooling channel 1806 can terminate prior to the end of the sleeve 1800. The drill channel 1803 can terminate at the distal opening 1812 and the suction channel can terminate at the suction inlet 1815. As will be understood, the sleeve 1800 can include some or all of the features shown and/or described with respect to the sleeve 100 (e.g., as illustrated by FIGS. 1-10) and/or the sleeve 1100 (e.g., as illustrated by FIGS. 11-17).

Figure 19:
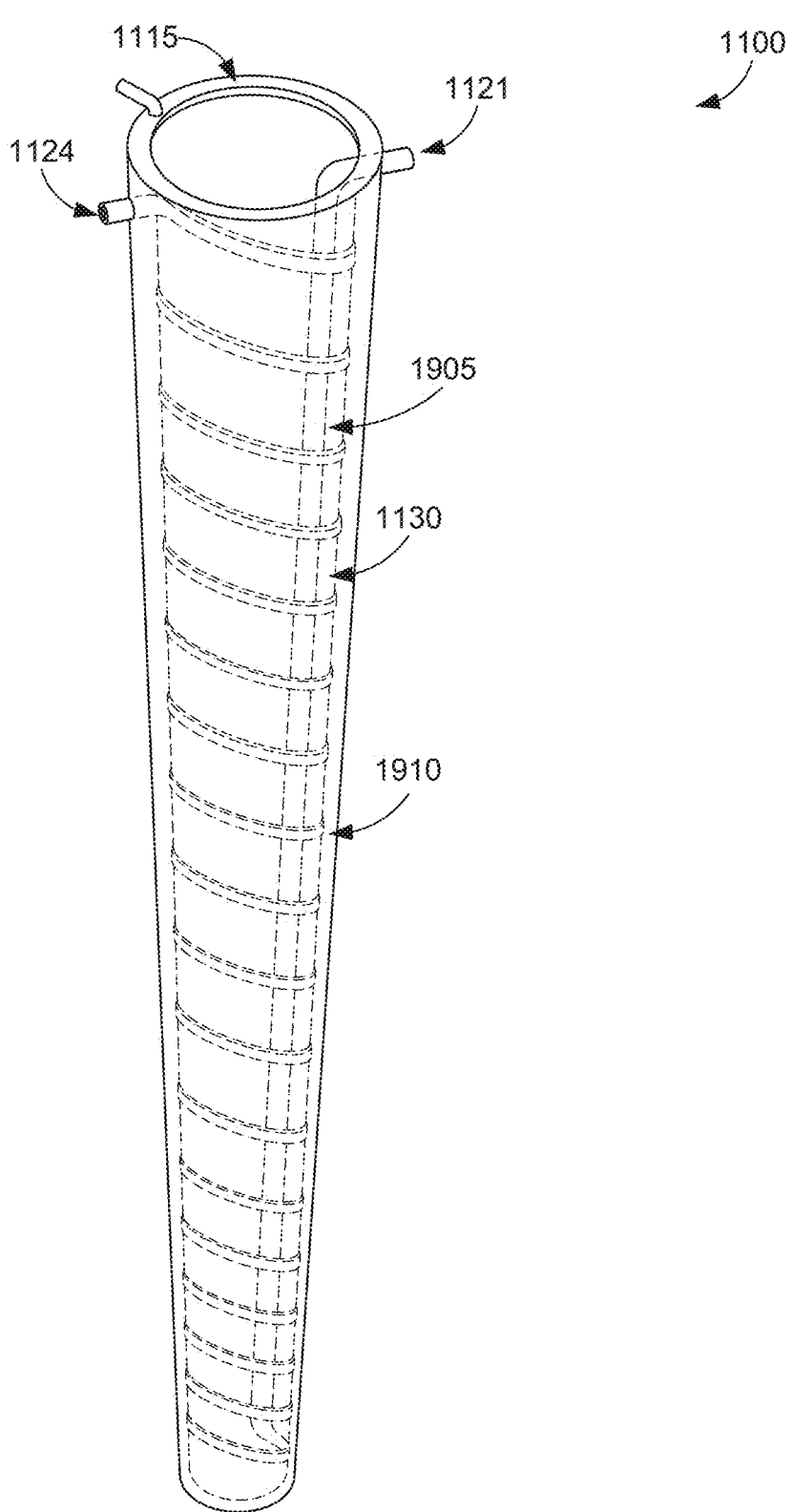
FIG. 19 illustrates a transparent side view of an exemplary sleeve, in accordance with the disclosed technology.

Referring now to FIG. 19, a transparent side view of exemplary sleeve 1100 is shown. The sleeve can include the drill channel 1115, the suction channel 1130, and the cooling channel 1127. The cooling channel 1127 can include a longitudinal portion 1905 and a helical portion 1910. The longitudinal portion 1905 can be in fluid connection with the fluid inlet connection point 1121 (e.g., the longitudinal portion 1905 can receive refrigerant from the fluid inlet connection point 1121). The longitudinal portion 1905 can extend from the top of the sleeve 1100 to the bottom of the sleeve 1100 and be located radially inward from the helical portion 1910. The longitudinal portion 1905 can fluidly connect to the helical portion 1910 towards the bottom of the sleeve 1100. The helical portion 1910 can extend helical from the bottom of the sleeve 1100 to the top of the sleeve 1100. The helical portion 1910 can be in fluid connection with the fluid outlet connection point 1124 (e.g., the helical portion 1910 can direct the refrigerant to the fluid outlet connection point 1124).

The drill channel 1115 can be located at the center of the sleeve 1100 and have a circular shape. The drill channel 1115 can extend the length of the sleeve 1100. The suction channel 1130 can be a concentric channel located on the outside of the drill channel 1115 and radially inward from the cooling channel 1127.

While various aspects have been described in the context of a preferred embodiment, additional aspects, features, and methodologies of the claimed device will be readily discernible from the description herein, by those of ordinary skill in the art. Many embodiments and adaptations of the disclosure and claimed device other than those herein described, as well as many variations, modifications, and equivalent arrangements and methodologies, will be apparent from or reasonably suggested by the disclosure and the foregoing description thereof, without departing from the substance or scope of the claims.

Aspects, features, and benefits of the claimed devices and methods for using the same will become apparent from the information disclosed in the exhibits and the other applications as incorporated by reference. Variations and modifications to the disclosed systems and methods may be effected without departing from the spirit and scope of the novel concepts of the disclosure.

It will, nevertheless, be understood that no limitation of the scope of the disclosure is intended by the information disclosed in the exhibits or the applications incorporated by reference; any alterations and further modifications of the described or illustrated embodiments, and any further applications of the principles of the disclosure as illustrated therein are contemplated as would normally occur to one skilled in the art to which the disclosure relates.

The foregoing description of the exemplary embodiments has been presented only for the purposes of illustration and description and is not intended to be exhaustive or to limit the devices and methods for using the same to the precise forms disclosed. Many modifications and variations are possible in light of the above teaching.

The embodiments were chosen and described in order to explain the principles of the devices and methods for using the same and their practical application so as to enable others skilled in the art to utilize the devices and methods for using the same and various embodiments and with various modifications as are suited to the particular use contemplated. Alternative embodiments will become apparent to those skilled in the art to which the present devices and methods for using the same pertain without departing from their spirit and scope. Accordingly, the scope of the present devices and methods for using the same is defined by the appended claims rather than the foregoing description and the exemplary embodiments described therein.

Clause 1: A cooling sleeve detachably attachable to a surgical drill, the cooling sleeve comprising: a sleeve body having: a proximal end and a distal end, the proximal end having an external dimeter that is greater than an external diameter of the distal end; an outermost annular sidewall, an innermost annular sidewall, and an intermediate annular sidewall; a first annular space defined between the outermost annular sidewall and the intermediate annular sidewall; a second annular space defined between the innermost annular sidewall and the intermediate annular sidewall; a hollow core defined at least in part by the innermost annular sidewall, wherein the hollow core is configured to receive at least a portion for the surgical drill such that a drill bit of the surgical drill extends through a distal opening at the distal end of the sleeve body; one of the first annular space or the second annular space is configured to provide a suction pathway to thereby remove material from a location proximate the distal end of the sleeve body toward the proximal end of the sleeve body; and another of the first annular space or the second annular space is configured to provide a refrigerant pathway to thereby circulate refrigerant material along at least a portion of the length of the body of the sleeve body, the refrigerant pathway configured to be in fluid communication with a refrigerant source.

Clause 2: The cooling sleeve of clause 1, wherein the refrigerant material is a gas.

Clause 3: The cooling sleeve of clause 1, wherein the refrigerant material is in fluid communication with a heat exchanger system.

Clause 4: The cooling sleeve of clause 1, wherein the suction pathway is in fluid communication with a vacuum system.

Clause 5: The cooling sleeve of clause 1, wherein the suction pathway is located radially inward from the refrigerant pathway.

Clause 6: The cooling sleeve of clause 1, wherein the refrigerant pathway is located radially inward from the suction pathway.

Clause 7: The cooling sleeve of clause 6, wherein the intermediate wall terminates at a position along a length of the sleeve body that is inwardly located from a distal end of the innermost sidewall and a distal end of the outermost sidewall.

Clause 8: The cooling sleeve of clause 7, wherein a radial width of the refrigerant pathway is largest at a location between the termination point of the intermediate sidewall and the distal end of the innermost sidewall and/or the distal end of the outermost sidewall.

Clause 9: The cooling sleeve of clause 1, wherein the refrigerant pathway has a generally helical path along the length of the sleeve body.

Clause 10: The cooling sleeve of clause 1, wherein the at least one of the refrigerant pathway or the suction pathway is approximately parallel to the outermost sidewall.

Clause 11: The cooling sleeve of clause 1, wherein the at least one of the refrigerant pathway or the suction pathway is approximately parallel to the innermost sidewall.

Clause 12: The cooling sleeve of clause 1, wherein the refrigerant pathway comprises a first longitudinal path, a second longitudinal path, and a plurality of latitudinal paths each fluidly connecting the first longitudinal path to the second longitudinal path.

Clause 13: The cooling sleeve of clause 12 further comprising a refrigerant inlet in fluid communication with one of the first or second longitudinal paths and a refrigerant outlet in fluid communication with another of the first or second longitudinal paths.

Clause 14: The cooling sleeve of clause 1, wherein: the intermediate wall is a first intermediate wall; the refrigerant pathway comprises a first longitudinal path and a second longitudinal path separated from the first longitudinal path by a second intermediate wall that is located radially outward from the first intermediate wall, wherein one of the first or second longitudinal paths is configured to direct a flow of the refrigerant material in a first direction extending from the proximal end toward the distal end, and another of the first or second longitudinal paths is configured to direct the flow of the refrigerant material in a second direction extending from the distal end toward the proximal end.

Clause 15: The cooling sleeve of clause 1, wherein the refrigerant pathway comprises a generally sinusoidal flow path.

Clause 16: The cooling sleeve of clause 15, wherein the generally sinusoidal flow path comprises a plurality of generally longitudinal flow path portions and a plurality of bends, each of the plurality of bends extending at least partially in a circumferential direction and fluidly connecting a pair of adjacent longitudinal path portions.

Clause 17: The cooling sleeve of clause 1, wherein the sleeve body has a proximal section and a distal section separated by a tapered section, the proximal section having a first exterior diameter and the distal section having a second exterior diameter that is less than the first exterior diameter.

Clause 18: The cooling sleeve of clause 1 further comprising a refrigerant inlet located at or near the proximal end of the sleeve body and a refrigerant outlet located at or near the proximal end of the sleeve body, wherein: the other of the first annular space or the second annular space is divided in half at the proximal end of cooling sleeve and at the distal end of the cooling sleeve to thereby define a plurality of semi-circular channels comprising an upper inlet portion, a lower inlet portion, a lower outlet portion, and an upper outlet portion, the upper inlet portion being directly fluidly connected to the refrigerant inlet and the upper outlet portion being directly fluidly connected to the refrigerant outlet.

Clause 19: The cooling sleeve of clause 18 further comprising an inlet crossover portion and an outlet crossover portion, wherein: the inlet crossover portion fluidly connects the upper inlet portion to the lower inlet portion and provides a flow path that extends approximately 180 degrees along a circumference of the other of the first annular space or the second annular space, such that the lower inlet portion is located on approximately the opposite side of the cooling sleeve from the upper inlet portion; and the outlet crossover portion fluidly connects the upper outlet portion to the lower outlet portion and provides a flow path that extends approximately 180 degrees along the circumference of the other of the first annular space or the second annular space, such that the lower outlet portion is located on approximately the opposite side of the cooling sleeve from the upper outlet portion.

Clause 20: The cooling sleeve of clause 1, wherein the refrigerant pathway comprises: a first refrigerant pathway portion extending longitudinally in a direction from the proximal end of the cooling sleeve toward the distal end of the cooling sleeve; and a second refrigerant pathway portion fluidly connected to the first refrigerant pathway portion and extending helically in a direction from the distal end of the cooling sleeve toward the proximal end of the cooling sleeve, wherein the first refrigerant pathway portion is located radially inward from the second refrigerant pathway portion and the refrigerant pathway is configured to sequentially direct refrigerant from an inlet of the cooling sleeve, through the first refrigerant pathway portion, through the second refrigerant pathway portion, and to an outlet of the cooling sleeve.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the scope of the present invention, are contemplated thereby for all purposes, and are intended to be covered by the following non-limiting claims.

What is claimed is:
1. A cooling sleeve detachably attachable to a surgical drill, the cooling sleeve comprising:
a sleeve body having:
a proximal end and a distal end, the proximal end having an external diameter that is greater than an external diameter of the distal end;
an outermost annular sidewall, an innermost annular sidewall, and an intermediate annular sidewall, wherein the intermediate annular sidewall terminates at a position along a length of the sleeve body that is inwardly located from a distal end of the innermost annular sidewall and a distal end of the outermost annular sidewall;
a first annular space defined between the outermost annular sidewall and the intermediate annular sidewall;
a second annular space defined between the innermost annular sidewall and the intermediate annular sidewall;
a hollow core defined at least in part by the innermost annular sidewall, wherein the hollow core is configured to receive at least a portion of the surgical drill such that a drill bit of the surgical drill extends through a distal opening at the distal end of the sleeve body;
one of the first annular space or the second annular space is configured to provide a suction pathway to thereby remove material from a location proximate the distal end of the sleeve body toward the proximal end of the sleeve body; and
another of the first annular space or the second annular space is configured to provide a refrigerant pathway to thereby circulate refrigerant material along at least a portion of the length of the sleeve body, wherein the refrigerant pathway is configured to be in fluid communication with a refrigerant source and is located radially inward from the suction pathway.
2. The cooling sleeve of claim 1, wherein the refrigerant material is a gas.
3. The cooling sleeve of claim 1, wherein the refrigerant material is in fluid communication with a heat exchanger system.
4. The cooling sleeve of claim 1, wherein the suction pathway is in fluid communication with a vacuum system.
5. The cooling sleeve of claim 1, wherein the suction pathway is located radially inward from the refrigerant pathway.
6. The cooling sleeve of claim 1, wherein a radial width of the refrigerant pathway is largest at a location between the position of the intermediate sidewall and the distal end of the innermost sidewall and/or the distal end of the outermost sidewall.
7. The cooling sleeve of claim 1, wherein at least one of the refrigerant pathway or the suction pathway is approximately parallel to the outermost sidewall.
8. The cooling sleeve of claim 1, wherein at least one of the refrigerant pathway or the suction pathway is approximately parallel to the innermost sidewall.
9. The cooling sleeve of claim 1, wherein the sleeve body has a proximal section and a distal section separated by a tapered section, the proximal section having a first exterior diameter and the distal section having a second exterior diameter that is less than the first exterior diameter.
10. A cooling sleeve detachably attachable to a surgical drill, the cooling sleeve comprising:
a sleeve body having:
a proximal end and a distal end, the proximal end having an external diameter that is greater than an external diameter of the distal end;
an outermost annular sidewall, an innermost annular sidewall, and an intermediate annular sidewall;
a first annular space defined between the outermost annular sidewall and the intermediate annular sidewall;
a second annular space defined between the innermost annular sidewall and the intermediate annular sidewall;

a hollow core defined at least in part by the innermost annular sidewall, wherein the hollow core is configured to receive at least a portion of the surgical drill such that a drill bit of the surgical drill extends through a distal opening at the distal end of the sleeve body;

one of the first annular space or the second annular space is configured to provide a suction pathway to thereby remove material from a location proximate the distal end of the sleeve body toward the proximal end of the sleeve body; and another of the first annular space or the second annular space is configured to provide a refrigerant pathway to thereby circulate refrigerant material along at least a portion of a length of the sleeve body, wherein the refrigerant pathway is configured to be in fluid communication with a refrigerant source and has a generally helical path along the length of the sleeve body.

11. A cooling sleeve detachably attachable to a surgical drill, the cooling sleeve comprising:

a sleeve body having:

a proximal end and a distal end, the proximal end having an external diameter that is greater than an external diameter of the distal end;

an outermost annular sidewall, an innermost annular sidewall, and an intermediate annular sidewall;

a first annular space defined between the outermost annular sidewall and the intermediate annular sidewall;

a second annular space defined between the innermost annular sidewall and the intermediate annular sidewall;

a hollow core defined at least in part by the innermost annular sidewall, wherein the hollow core is configured to receive at least a portion of the surgical drill such that a drill bit of the surgical drill extends through a distal opening at the distal end of the sleeve body;

one of the first annular space or the second annular space is configured to provide a suction pathway to thereby remove material from a location proximate the distal end of the sleeve body toward the proximal end of the sleeve body; and another of the first annular space or the second annular space is configured to provide a refrigerant pathway to thereby circulate refrigerant material along at least a portion of a length of the sleeve body, wherein the refrigerant pathway is configured to be in fluid communication with a refrigerant source and comprises a first longitudinal path, a second longitudinal path, and a plurality of latitudinal paths each fluidly connecting the first longitudinal path to the second longitudinal path.

12. The cooling sleeve of claim 11 further comprising a refrigerant inlet in fluid communication with one of the first or second longitudinal paths and a refrigerant outlet in fluid communication with another of the first or second longitudinal paths.

13. A cooling sleeve detachably attachable to a surgical drill, the cooling sleeve comprising:

a sleeve body having:

a proximal end and a distal end, the proximal end having an external diameter that is greater than an external diameter of the distal end;

an outermost annular sidewall, an innermost annular sidewall, and a first intermediate annular sidewall;

a first annular space defined between the outermost annular sidewall and the first intermediate annular sidewall;

a second annular space defined between the innermost annular sidewall and the first intermediate annular sidewall;

a hollow core defined at least in part by the innermost annular sidewall, wherein the hollow core is configured to receive at least a portion of the surgical drill such that a drill bit of the surgical drill extends through a distal opening at the distal end of the sleeve body:

one of the first annular space or the second annular space is configured to provide a suction pathway to thereby remove material from a location proximate the distal end of the sleeve body toward the proximal end of the sleeve body; and another of the first annular space or the second annular space is configured to provide a refrigerant pathway to thereby circulate refrigerant material along at least a portion of a length of the sleeve body, wherein:

the refrigerant pathway is configured to be in fluid communication with a refrigerant source;

the refrigerant pathway comprises a first longitudinal path and a second longitudinal path separated from the first longitudinal path by a second intermediate wall that is located radially outward from the first intermediate annular sidewall; and one of the first or second longitudinal paths is configured to direct a flow of the refrigerant material in a first direction extending from the proximal end toward the distal end, and another of the first or second longitudinal paths is configured to direct the flow of the refrigerant material in a second direction extending from the distal end toward the proximal end.

14. A cooling sleeve detachably attachable to a surgical drill, the cooling sleeve comprising:

a sleeve body having:

a proximal end and a distal end, the proximal end having an external diameter that is greater than an external diameter of the distal end;

an outermost annular sidewall, an innermost annular sidewall, and an intermediate annular sidewall;

a first annular space defined between the outermost annular sidewall and the intermediate annular sidewall;

a second annular space defined between the innermost annular sidewall and the intermediate annular sidewall;

a hollow core defined at least in part by the innermost annular sidewall, wherein the hollow core is configured to receive at least a portion of the surgical drill such that a drill bit of the surgical drill extends through a distal opening at the distal end of the sleeve body;

one of the first annular space or the second annular space is configured to provide a suction pathway to thereby remove material from a location proximate the distal end of the sleeve body toward the proximal end of the sleeve body; and another of the first annular space or the second annular space is configured to provide a refrigerant pathway to thereby circulate refrigerant material along at least a portion of a length of the sleeve body, wherein the refrigerant pathway is configured to be in fluid communication with a refrigerant source and comprises a generally sinusoidal flow path.

15. The cooling sleeve of claim 14, wherein the generally sinusoidal flow path comprises a plurality of generally longitudinal flow path portions and a plurality of bends, each of the plurality of bends extending at least partially in a circumferential direction and fluidly connecting a pair of adjacent longitudinal path portions.

16. A cooling sleeve detachably attachable to a surgical drill, the cooling sleeve comprising:
  a sleeve body having:
    a proximal end and a distal end, the proximal end having an external diameter that is greater than an external diameter of the distal end;
    an outermost annular sidewall, an innermost annular sidewall, and an intermediate annular sidewall;
    a first annular space defined between the outermost annular sidewall and the intermediate annular sidewall;
    a second annular space defined between the innermost annular sidewall and the intermediate annular sidewall;
    a hollow core defined at least in part by the innermost annular sidewall, wherein the hollow core is configured to receive at least a portion of the surgical drill such that a drill bit of the surgical drill extends through a distal opening at the distal end of the sleeve body;
    one of the first annular space or the second annular space is configured to provide a suction pathway to thereby remove material from a location proximate the distal end of the sleeve body toward the proximal end of the sleeve body;
    another of the first annular space or the second annular space is configured to provide a refrigerant pathway to thereby circulate refrigerant material along at least a portion of a length of the sleeve body, wherein the refrigerant pathway is configured to be in fluid communication with a refrigerant source; and
    a refrigerant inlet located at or near the proximal end of the sleeve body and a refrigerant outlet located at or near the proximal end of the sleeve body, wherein:
    at least one of the first annular space or the second annular space is divided in half at the proximal end of the cooling sleeve and at the distal end of the cooling sleeve to thereby define a plurality of semicircular channels comprising an upper inlet portion, a lower inlet portion, a lower outlet portion, and an upper outlet portion, the upper inlet portion being directly fluidly connected to the refrigerant inlet and the upper outlet portion being directly fluidly connected to the refrigerant outlet.

17. The cooling sleeve of claim 16 further comprising an inlet crossover portion and an outlet crossover portion, wherein:
  the inlet crossover portion fluidly connects the upper inlet portion to the lower inlet portion and provides a flow path that extends approximately 180 degrees along a circumference of the other of the first annular space or the second annular space, such that the lower inlet portion is located on approximately a first opposite side of the cooling sleeve from the upper inlet portion; and
  the outlet crossover portion fluidly connects the upper outlet portion to the lower outlet portion and provides a flow path that extends approximately 180 degrees along the circumference of at least one the other of the first annular space or the second annular space, such that the lower outlet portion is located on approximately a second opposite side of the cooling sleeve from the upper outlet portion.

18. A cooling sleeve o detachable to a surgical drill, the cooling sleeve comprising:
  a sleeve body having:
    a proximal end and a distal end, the proximal end having an external diameter that is greater than an external diameter of the distal end;
    an outermost annular sidewall, an innermost annular sidewall, and an intermediate annular sidewall;
    a first annular space defined between the outermost annular sidewall and the intermediate annular sidewall;
    a second annular space defined between the innermost annular sidewall and the intermediate annular sidewall;
    a hollow core defined at least in part by the innermost annular sidewall, wherein the hollow core is configured to receive at least a portion of the surgical drill such that a drill bit of the surgical drill extends through a distal opening at the distal end of the sleeve body;
    one of the first annular space or the second annular space is configured to provide a suction pathway to thereby remove material from a location proximate the distal end of the sleeve body toward the proximal end of the sleeve body; and
    another of the first annular space or the second annular space is configured to provide a refrigerant pathway to thereby circulate refrigerant material along at least a portion of a length of the sleeve body, wherein the refrigerant pathway is configured to be in fluid communication with a refrigerant source and comprises:
    a first refrigerant pathway portion extending longitudinally in a direction from the proximal end of the cooling sleeve toward the distal end of the cooling sleeve; and
    a second refrigerant pathway portion fluidly connected to the first refrigerant pathway portion and extending helically in a direction from the distal end of the cooling sleeve toward the proximal end of the cooling sleeve,
    wherein the first refrigerant pathway portion is located radially inward from the second refrigerant pathway portion and the refrigerant pathway is configured to sequentially direct refrigerant from an inlet of the cooling sleeve, through the first refrigerant pathway portion, through the second refrigerant pathway portion, and to an outlet of the cooling sleeve.

* * * * *